US012392777B2

(12) United States Patent
Sulea et al.

(10) Patent No.: US 12,392,777 B2
(45) Date of Patent: Aug. 19, 2025

(54) ANTIBODY VARIANTS WITH pH-DEPENDENT ANTIGEN BINDING FOR SELECTIVE TARGETING OF SOLID TUMORS

(71) Applicant: National Research Council of Canada, Ottawa (CA)

(72) Inventors: Traian Sulea, Kirkland (CA); Jason Baardsnes, Montreal (CA); Christopher R. Corbeil, Dollard-des-Ormeaux (CA); Maria L. Jaramillo, Beaconsfield (CA); Enrico O. Purisima, Pierrefonds (CA); John C. Zwaagstra, Laval (CA); Nazanin Larijani Rohani, Montreal (CA)

(73) Assignee: National Research Council of Canada, Ottawa (CA)

( * ) Notice: Subject to any disclaimer, the term of this patent is extended or adjusted under 35 U.S.C. 154(b) by 954 days.

(21) Appl. No.: 17/600,805

(22) PCT Filed: Mar. 30, 2020

(86) PCT No.: PCT/IB2020/053024
§ 371 (c)(1),
(2) Date: Oct. 1, 2021

(87) PCT Pub. No.: WO2020/201992
PCT Pub. Date: Oct. 8, 2020

(65) Prior Publication Data
US 2022/0162337 A1  May 26, 2022

Related U.S. Application Data

(60) Provisional application No. 62/828,024, filed on Apr. 2, 2019.

(51) Int. Cl.
*G01N 33/574* (2006.01)
*A61K 47/68* (2017.01)
*A61P 35/00* (2006.01)
*C07K 16/32* (2006.01)

(52) U.S. Cl.
CPC . *G01N 33/57415* (2013.01); *A61K 47/68033* (2023.08); *A61K 47/6855* (2017.08); *C07K 16/32* (2013.01); *A61P 35/00* (2018.01); *C07K 2317/24* (2013.01); *C07K 2317/31* (2013.01); *C07K 2317/35* (2013.01); *C07K 2317/55* (2013.01); *C07K 2317/77* (2013.01); *C07K 2317/92* (2013.01); *C07K 2319/33* (2013.01)

(58) Field of Classification Search
CPC ......... G01N 33/57415; G01N 2333/71; A61K 47/68033; A61K 47/6855; C07K 16/32; C07K 2317/24; C07K 2317/31; C07K 2317/35; C07K 2317/55; C07K 2317/77; C07K 2317/92; C07K 2319/33; C07K 2317/565; C07K 2317/76; A61P 35/00
See application file for complete search history.

(56) References Cited

U.S. PATENT DOCUMENTS

2013/0266564 A1  10/2013  Jaramillo et al.

FOREIGN PATENT DOCUMENTS

| WO | WO 1995/004069 A1 | 2/1995 |
| WO | WO 2003/046560 A3 | 9/2003 |
| WO | WO 2004/076670 A1 | 9/2004 |
| WO | WO 2008/027236 A2 | 3/2008 |
| WO | WO 2010/027981 A1 | 3/2010 |
| WO | WO 2010/108127 A1 | 9/2010 |
| WO | WO 2012/075581 A1 | 6/2012 |
| WO | WO 2012/100346 A1 | 8/2012 |
| WO | WO 2015/095539 A1 | 6/2015 |

OTHER PUBLICATIONS

Alberts, B. Molecular Biology of the Cell (Chapters 6 and 7). 6th Edition, Garland Science, Taylor and Francis Group, New York. 2015 (Year: 2015).*
Nguyen AW, et al. Enhancing the immunotherapeutic Trastuzumab for selective activity in the low pH tumor microenvironment. J Immunol May 1, 2018; 200 (1_Supplement): 58.16. https://doi.org/10.4049/jimmunol.200.Supp.58.16 (Year: 2018).*
Hunter M, et al. Optimization of Protein Expression in Mammalian Cells. Curr Protoc Protein Sci. Feb. 2019;95(1):e77. doi: 10.1002/cpps.77. Epub Sep. 28, 2018. PMID: 30265450. (Year: 2019).*
Bailey et al., Applications for an engineered Protein-G variant with a pH controllable affinity to antibody fragments. J Immunol Methods. Dec. 15, 2014;415:24-30. doi: 10.1016/j.jim.2014.10.003. Epub Oct. 22, 2014.
Beck et al., Strategies and challenges for the next generation of antibody-drug conjugates. Nat Rev Drug Discov. May 2017;16(5):315-337. doi: 10.1038/nrd.2016.268. Epub Mar. 17, 2017.
Bonvin et al., De novo isolation of antibodies with pH-dependent binding properties. MAbs. 2015;7(2):294-302. doi: 10.1080/19420862.2015.1006993.

(Continued)

*Primary Examiner* — Misook Yu
*Assistant Examiner* — Alec Jon Peters
(74) *Attorney, Agent, or Firm* — Wolf, Greenfield & Sacks, P.C.

(57) ABSTRACT

The present invention is directed to anti-Her2 antibodies and fragments thereof, compositions, and uses thereof. The antibodies and fragments thereof bind to Her2-expressing cells in a pH-dependent manner, with low affinity at the physiological pH typical of normal cells and tissues, and with high affinity at the slightly acidic pH characteristic to solid tumors. Furthermore, the antibodies inhibit the growth of tumor spheroids at a level comparable to that of the benchmark anti-Her2 antibody Herceptin at acidic pH, whereas these effects were significantly reduced at physiological pH. This pH selectivity of cellular growth inhibition is maintained upon antibody conjugation to cytotoxic drugs. The invention also includes methods of treating solid tumors, methods of detecting solid tumors, and methods of pH-dependent capturing of the Her-2 ectodomain.

20 Claims, 14 Drawing Sheets

Specification includes a Sequence Listing.

(56) References Cited

OTHER PUBLICATIONS

Bostrom et al., High affinity antigen recognition of the dual specific variants of herceptin is entropy-driven in spite of structural plasticity. PLoS One. Apr. 22, 2011;6(4):e17887. doi: 10.1371/journal.pone.0017887.

Bostrom et al., Variants of the antibody herceptin that interact with HER2 and VEGF at the antigen binding site. Science. Mar. 20, 2009;323(5921):1610-4. doi: 10.1126/science.1165480.

Brinkmann et al., The making of bispecific antibodies. MAbs. Feb./Mar. 2017;9(2):182-212. doi: 10.1080/19420862.2016.1268307.

Chaparro-Riggers et al., Increasing serum half-life and extending cholesterol lowering in vivo by engineering antibody with pH-sensitive binding to PCSK9. J Biol Chem. Mar. 30, 2012;287(14):11090-7. doi: 10.1074/jbc.M111.319764. Epub Jan. 31, 2012.

Chothia et al., Canonical structures for the hypervariable regions of immunoglobulins. J Mol Biol. Aug. 20, 1987;196(4):901-17. doi: 10.1016/0022-2836(87)90412-8.

Damaghi et al., pH sensing and regulation in cancer. Front Physiol. Dec. 17, 2013;4:370. doi: 10.3389/fphys.2013.00370.

De Kruif et al., Leucine zipper dimerized bivalent and bispecific scFv antibodies from a semi-synthetic antibody phage display library. J Biol Chem. Mar. 29, 1996;271(13):7630-4. doi: 10.1074/jbc.271.13.7630.

Devanaboyina et al., The effect of pH dependence of antibody-antigen interactions on subcellular trafficking dynamics. MAbs. Nov.-Dec. 2013;5(6):851-9. doi: 10.4161/mabs.26389.

Dotti et al., Design and development of therapies using chimeric antigen receptor-expressing T cells. Immunol Rev. Jan. 2014;257(1):107-26. doi: 10.1111/imr.12131. Author Manuscript. 35 pages.

Eisenberg et al., Analysis of membrane and surface protein sequences with the hydrophobic moment plot. J Mol Biol. Oct. 15, 1984;179(1):125-42. doi: 10.1016/0022-2836(84)90309-7.

Estrella et al., Acidity generated by the tumor microenvironment drives local invasion. Cancer Res. Mar. 1, 2013;73(5):1524-35. doi: 10.1158/0008-5472.CAN-12-2796. Epub Jan. 3, 2013.

Fukamachi et al., Tumor specific low pH environments enhance the cytotoxicity of lovastatin and cantharidin. Cancer Lett. Nov. 28, 2010;297(2):182-9. doi: 10.1016/j.canlet.2010.05.010. Epub Jun. 17, 2010.

Gera et al., Design of pH sensitive binding proteins from the hyperthermophilic Sso7d scaffold. PLoS One. 2012;7(11):e48928. doi: 10.1371/journal.pone.0048928. Epub Nov. 7, 2012. 14 pages.

Ghetie et al., Increasing the serum persistence of an IgG fragment by random mutagenesis. Nat Biotechnol. Jul. 1997;15(7):637-40. doi: 10.1038/nbt0797-637.

Gillies et al., MRI of the tumor microenvironment. J Magn Reson Imaging. Oct. 2002;16(4):430-50. doi: 10.1002/jmri.10181. Erratum in: J Magn Reson Imaging Dec. 2002;16(6):751.

Guerois et al., Predicting changes in the stability of proteins and protein complexes: a study of more than 1000 mutations. J Mol Biol. Jul. 5, 2002;320(2):369-87. doi: 10.1016/S0022-2836(02)00442-4.

Harms et al., Optimizing properties of antireceptor antibodies using kinetic computational models and experiments. Methods Enzymol. 2012;502:67-87. doi: 10.1016/B978-0-12-416039-2.00004-5.

Hashim et al., Imaging pH and metastasis. NMR Biomed. Jul. 2011;24(6):582-91. doi: 10.1002/nbm.1644. Epub Mar. 8, 2011. Author Manuscript. 19 pages.

Heinzelman et al., Engineering pH responsive fibronectin domains for biomedical applications. J Biol Eng. May 15, 2015;9:6. doi: 10.1186/s13036-015-0004-1. 11 pages.

Igawa et al., pH-dependent antigen-binding antibodies as a novel therapeutic modality. Biochim Biophys Acta. Nov. 2014;1844(11):1943-1950. doi: 10.1016/j.bbapap.2014.08.003. Epub Aug. 12, 2014.

Kabat et al., Identical V region amino acid sequences and segments of sequences in antibodies of different specificities. Relative contributions of VH and VL genes, minigenes, and complementarity-determining regions to binding of antibody-combining sites. J Immunol. Sep. 1, 1991;147(5):1709-19.

Kato et al., Acidic extracellular microenvironment and cancer. Cancer Cell Int. Sep. 3, 2013;13(1):89. doi: 10.1186/1475-2867-13-89. 8 pages.

Kelley et al., Thermodynamic analysis of an antibody functional epitope. Biochemistry. Jul. 13, 1993;32(27):6828-35. doi: 10.1021/bi00078a005.

Konning et al., Isolation of a pH-Sensitive IgNAR Variable Domain from a Yeast-Displayed, Histidine-Doped Master Library. Mar Biotechnol (NY). Apr. 2016;18(2):161-7. doi: 10.1007/s10126-016-9690-z. Epub Feb. 2, 2016.

Kontermann, Dual targeting strategies with bispecific antibodies. MAbs. Mar.-Apr. 2012;4(2):182-97. doi: 10.4161/mabs.4.2.19000. Epub Mar. 1, 2012.

Krivov et al., Improved prediction of protein side-chain conformations with SCWRL4. Proteins. Dec. 2009;77(4):778-95. doi: 10.1002/prot.22488.

Lefranc et al., IMGT unique numbering for immunoglobulin and T cell receptor variable domains and Ig superfamily V-like domains. Dev Comp Immunol. Jan. 2003;27(1):55-77. doi: 10.1016/s0145-305x(02)00039-3.

Lippow et al., Computational design of antibody-affinity improvement beyond in vivo maturation. Nat Biotechnol. Oct. 2007;25(10):1171-6. doi: 10.1038/nbt1336. Epub Sep. 23, 2007.

Masters et al., Clinical toxicity of antibody drug conjugates: a meta-analysis of payloads. Invest New Drugs. Feb. 2018;36(1):121-135. doi: 10.1007/s10637-017-0520-6. Epub Oct. 13, 2017.

Merritt et al., AB5 toxins. Curr Opin Struct Biol. Apr. 1995;5(2):165-71. doi: 10.1016/0959-440x(95)80071-9.

Murtaugh et al., A combinatorial histidine scanning library approach to engineer highly pH-dependent protein switches. Protein Sci. Sep. 2011;20(9):1619-31. doi: 10.1002/pro.696. Epub Aug. 3, 2011.

Naïm et al., Solvated interaction energy (SIE) for scoring protein-ligand binding affinities. 1. Exploring the parameter space. J Chem Inf Model. Jan.-Feb. 2007;47(1):122-33. doi: 10.1021/ci600406v.

Nelson et al., Antibody fragments: hope and hype. MAbs. Jan.-Feb. 2010;2(1):77-83. doi: 10.4161/mabs.2.1.10786. Epub Jan. 27, 2010.

Nguyen et al., Enhancing the immunotherapeutic Trastuzumab for selective activity in the low pH tumor microenvironment. J Immunol. May 1, 2018; 200(1 Supplement):58.16. 5 pages.

Ó Conchúir et al., A Web Resource for Standardized Benchmark Datasets, Metrics, and Rosetta Protocols for Macromolecular Modeling and Design. PLoS One. Sep. 3, 2015;10(9):e0130433. doi: 10.1371/journal.pone.0130433. 18 pages.

Onsum et al., Single-cell quantitative HER2 measurement identifies heterogeneity and distinct subgroups within traditionally defined HER2-positive patients. Am J Pathol. Nov. 2013;183(5):1446-1460. doi: 10.1016/j.ajpath.2013.07.015. Epub Sep. 11, 2013.

Ridgway et al., 'Knobs-into-holes' engineering of antibody CH3 domains for heavy chain heterodimerization. Protein Eng. Jul. 1996;9(7):617-21. doi: 10.1093/protein/9.7.617.

Rohl et al., Protein structure prediction using Rosetta. Methods Enzymol. 2004;383:66-93. doi: 10.1016/S0076-6879(04)83004-0.

Rudnick et al., Influence of affinity and antigen internalization on the uptake and penetration of Anti-HER2 antibodies in solid tumors. Cancer Res. Mar. 15, 2011;71(6):2250-9. doi: 10.1158/0008-5472.CAN-10-2277.

Sampson et al., Tumor-specific immunotherapy targeting the EGFRvIII mutation in patients with malignant glioma. Semin Immunol. Oct. 2008;20(5):267-75. doi: 10.1016/j.smim.2008.04.001. Epub Jun. 9, 2008.

Sarkar et al., Rational cytokine design for increased lifetime and enhanced potency using pH-activated "histidine switching". Nat Biotechnol. Sep. 2002;20(9):908-13. doi: 10.1038/nbt725. Epub Aug. 5, 2002.

Schröter et al., A generic approach to engineer antibody pH-switches using combinatorial histidine scanning libraries and yeast display. MAbs. 2015;7(1):138-51. doi: 10.4161/19420862.2014.985993.

Schymkowitz et al., The FoldX web server: an online force field. Nucleic Acids Res. Jul. 1, 2005;33(Web Server issue):W382-8. doi: 10.1093/nar/gki387.

(56) References Cited

OTHER PUBLICATIONS

Seijsing et al., An engineered affibody molecule with pH-dependent binding to FcRn mediates extended circulatory half-life of a fusion protein. Proc Natl Acad Sci U S A. Dec. 2, 2014;111(48):17110-5. doi: 10.1073/pnas.1417717111. Epub Nov. 18, 2014.

Shilova et al., Internalization and Recycling of the HER2 Receptor on Human Breast Adenocarcinoma Cells Treated with Targeted Phototoxic Protein DARPinminiSOG. Acta Naturae. Jul.-Sep. 2015;7(3):126-32.

Slaga et al., Avidity-based binding to HER2 results in selective killing of HER2-overexpressing cells by anti-HER2/CD3. Sci Transl Med. Oct. 17, 2018;10(463):eaat5775. doi: 10.1126/scitranslmed.aat5775.

Spassov et al., pH-selective mutagenesis of protein-protein interfaces: in silico design of therapeutic antibodies with prolonged half-life. Proteins. Apr. 2013;81(4):704-14. doi: 10.1002/prot.24230. Epub Jan. 15, 2013.

Spiess et al., Alternative molecular formats and therapeutic applications for bispecific antibodies. Mol Immunol. Oct. 2015;67(2 Pt A):95-106. doi: 10.1016/j.molimm.2015.01.003. Epub Jan. 27, 2015.

Strauch et al., Computational design of a pH-sensitive IgG binding protein. Proc Natl Acad Sci U S A. Jan. 14, 2014;111(2):675-80. doi: 10.1073/pnas.1313605111. Epub Dec. 31, 2013.

Stubb et al., Causes and consequences of tumour acidity and implications for treatment. Mol Med Today. Jan. 2000;6(1):15-9. doi: 10.1016/s1357-4310(99)01615-9.

Sulea et al., Application of Assisted Design of Antibody and Protein Therapeutics (ADAPT) improves efficacy of a Clostridium difficile toxin A single-domain antibody. Sci Rep. Feb. 2, 2018;8(1):2260. doi: 10.1038/s41598-018-20599-4.

Sulea et al., Assessment of Solvated Interaction Energy Function for Ranking Antibody-Antigen Binding Affinities. J Chem Inf Model. Jul. 25, 2016;56(7):1292-303. doi: 10.1021/acs.jcim.6b00043. Epub Jul. 14, 2016.

Sulea et al., Structure-based engineering of pH-dependent antibody binding for selective targeting of solid-tumor microenvironment. MAbs. Jan.-Dec. 2020;12(1):1682866. doi: 10.1080/19420862.2019.1682866. 15 pages.

Sulea et al., The solvated interaction energy method for scoring binding affinities. Methods Mol Biol. 2012;819:295-303. doi: 10.1007/978-1-61779-465-0_19.

Tannock et al., Acid pH in tumors and its potential for therapeutic exploitation. Cancer Res. Aug. 15, 1989;49(16):4373-84.

Tanokura, 1H-NMR study on the tautomerism of the imidazole ring of histidine residues. I. Microscopic pK values and molar ratios of tautomers in histidine-containing peptides. Biochim Biophys Acta. Feb. 15, 1983;742(3):576-85. doi: 10.1016/0167-4838(83)90276-5.

Tillotson et al., Engineering an Anti-Transferrin Receptor ScFv for pH-Sensitive Binding Leads to Increased Intracellular Accumulation. PLoS One. Dec. 29, 2015;10(12):e0145820. doi: 10.1371/journal.pone.0145820.

Traxlmayr et al., Construction of pH-sensitive Her2-binding IgG1-Fc by directed evolution. Biotechnol J. Aug. 2014;9(8):1013-22. doi: 10.1002/biot.201300483.

Tsukamoto et al., Engineered protein A ligands, derived from a histidine-scanning library, facilitate the affinity purification of IgG under mild acidic conditions. J Biol Eng. Jul. 1, 2014;8:15. doi: 10.1186/1754-1611-8-15. 9 pages.

Vivcharuk et al., Assisted Design of Antibody and Protein Therapeutics (ADAPT). PLoS One. Jul. 27, 2017;12(7):e0181490. doi: 10.1371/journal.pone.0181490. 17 pages.

Zhang et al., Pentamerization of single-domain antibodies from phage libraries: a novel strategy for the rapid generation of high-avidity antibody reagents. J Mol Biol. Jan. 2, 2004;335(1):49-56. doi: 10.1016/j.jmb.2003.09.034.

Zhang et al., Tumor pH and its measurement. J Nucl Med. Aug. 2010;51(8):1167-70. doi: 10.2967/jnumed.109.068981. Epub Jul. 21, 2010.

Zhou et al., Impact of intrinsic affinity on functional binding and biological activity of EGFR antibodies. Mol Cancer Ther. Jul. 2012;11(7):1467-76. doi: 10.1158/1535-7163.MCT-11-1038. Epub May 7, 2012.

[No Author Listed], 3BE1—Dual specific bH1 Fab in complex with the extracellular domain of HER2/ErbB-2. Nov. 18, 2008. doi: 10.2210/pdb3be1/pdb. Retrieved from <https://pdbj.org/mine/summary/3be1> on Nov. 7, 2022. 4 pages.

PCT/IB2020/053024, Jun. 23, 2020, International Search Report and Written Opinion.

PCT/IB2020/053024, Oct. 14, 2021, International Preliminary Report on Patentability.

* cited by examiner

SEQUENCE LISTING

<160> NUMBER OF SEQ ID NOS: 22

<210> SEQ ID NO 1
<211> LENGTH: 10
<212> TYPE: PRT
<213> ORGANISM: Artificial Sequence
<220> FEATURE:
<223> OTHER INFORMATION: CDR-H1

<400> SEQUENCE: 1

Gly Phe Asn Ile Lys Asp Thr Tyr Ile His
1               5                   10

<210> SEQ ID NO 2
<211> LENGTH: 17
<212> TYPE: PRT
<213> ORGANISM: Artificial Sequence
<220> FEATURE:
<223> OTHER INFORMATION: CDR-H2

<400> SEQUENCE: 2

Arg Ile Tyr Pro Thr Asn Gly Tyr Thr His Tyr Ala Asp Ser Val Lys
1               5                   10                  15

Gly

<210> SEQ ID NO 3
<211> LENGTH: 11
<212> TYPE: PRT
<213> ORGANISM: Artificial Sequence
<220> FEATURE:
<223> OTHER INFORMATION: CDR-H3

<400> SEQUENCE: 3

Trp Gly Gly Asp Gly Phe Tyr Ala Met Asp Tyr
1               5                   10

<210> SEQ ID NO 4
<211> LENGTH: 15
<212> TYPE: PRT
<213> ORGANISM: Artificial Sequence
<220> FEATURE:
<223> OTHER INFORMATION: CDR-L1-generic
<220> FEATURE:
<221> NAME/KEY: MISC_FEATURE
<222> LOCATION: (8)..(8)
<223> OTHER INFORMATION: where X is R or H
<220> FEATURE:
<221> NAME/KEY: MISC_FEATURE
<222> LOCATION: (9)..(9)
<223> OTHER INFORMATION: where X is S or H

<400> SEQUENCE: 4

Arg Ala Ser Gln Asp Ile Pro Xaa Xaa Ile Ser Gly Tyr Val Ala
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: CDR-L2

<400> SEQUENCE: 5

Trp Gly Ser Tyr Leu Tyr Ser
1               5

```
<210> SEQ ID NO 6
<211> LENGTH: 9
<212> TYPE: PRT
<213> ORGANISM: Artificial Sequence
<220> FEATURE:
<223> OTHER INFORMATION: CDR-L3

<400> SEQUENCE: 6

Gln Gln His Tyr Thr Thr Pro Pro Thr
1               5

<210> SEQ ID NO 7
<211> LENGTH: 15
<212> TYPE: PRT
<213> ORGANISM: Artificial Sequence
<220> FEATURE:
<223> OTHER INFORMATION: CDR-L1-v1

<400> SEQUENCE: 7

Arg Ala Ser Gln Asp Ile Pro Arg Ser Ile Ser Gly Tyr Val Ala
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: CDR-L1-v2

<400> SEQUENCE: 8

Arg Ala Ser Gln Asp Ile Pro His Ser Ile Ser Gly Tyr Val Ala
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: CDR-L1-v3

<400> SEQUENCE: 9

Arg Ala Ser Gln Asp Ile Pro Arg His Ile Ser Gly Tyr Val Ala
1               5                   10                  15

<210> SEQ ID NO 10
<211> LENGTH: 120
<212> TYPE: PRT
<213> ORGANISM: Artificial Sequence
<220> FEATURE:
<223> OTHER INFORMATION: bH1-P5-Fv

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr His Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

```
Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 11
<211> LENGTH: 111
<212> TYPE: PRT
<213> ORGANISM: Artificial Sequence
<220> FEATURE:
<223> OTHER INFORMATION: bH1-P5-Fv

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Pro Arg Ser
            20                  25                  30

Ile Ser Gly Tyr Val Ala Trp Tyr Gln Gln Lys Pro Gly Lys Ala Pro
        35                  40                  45

Lys Leu Leu Ile Tyr Trp Gly Ser Tyr Leu Tyr Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Thr Thr Pro Pro Thr Phe Gly Gln Gly Thr Lys Val Glu Ile Lys
            100                 105                 110

<210> SEQ ID NO 12
<211> LENGTH: 111
<212> TYPE: PRT
<213> ORGANISM: Artificial Sequence
<220> FEATURE:
<223> OTHER INFORMATION: bH1-P5P7-Fv

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Pro His Ser
            20                  25                  30

Ile Ser Gly Tyr Val Ala Trp Tyr Gln Gln Lys Pro Gly Lys Ala Pro
        35                  40                  45

Lys Leu Leu Ile Tyr Trp Gly Ser Tyr Leu Tyr Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Thr Thr Pro Pro Thr Phe Gly Gln Gly Thr Lys Val Glu Ile Lys
            100                 105                 110

<210> SEQ ID NO 13
<211> LENGTH: 111
<212> TYPE: PRT
<213> ORGANISM: Artificial Sequence
<220> FEATURE:
<223> OTHER INFORMATION: bH1-P5P8-Fv

<400> SEQUENCE: 13
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Pro Arg His
            20                  25                  30

Ile Ser Gly Tyr Val Ala Trp Tyr Gln Gln Lys Pro Gly Lys Ala Pro
            35                  40                  45

Lys Leu Leu Ile Tyr Trp Gly Ser Tyr Leu Tyr Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Thr Thr Pro Pro Thr Phe Gly Gln Gly Thr Lys Val Glu Ile Lys
            100                 105                 110
```

<210> SEQ ID NO 14
<211> LENGTH: 245
<212> TYPE: PRT
<213> ORGANISM: Artificial Sequence
<220> FEATURE:
<223> OTHER INFORMATION: bH1-P5-Fab

<400> SEQUENCE: 14

```
Met Asp Trp Thr Trp Arg Ile Leu Phe Leu Val Ala Ala Ala Thr Gly
1               5                   10                  15

Thr His Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
            35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr His Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
            115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
            210                 215                 220

Asn His Lys Pro Ser Asn Thr Lys Val Asp Lys Lys Val Glu Pro Lys
225                 230                 235                 240

Ser Cys Asp Lys Thr
                245
```

<210> SEQ ID NO 15
<211> LENGTH: 238
<212> TYPE: PRT
<213> ORGANISM: Artificial Sequence
<220> FEATURE:
<223> OTHER INFORMATION: bH1-P5-Fab

<400> SEQUENCE: 15

```
Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Pro Arg Ser Ile Ser Gly Tyr Val Ala Trp Tyr Gln Gln Lys Pro
    50                  55                  60

Gly Lys Ala Pro Lys Leu Leu Ile Tyr Trp Gly Ser Tyr Leu Tyr Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Tyr Cys
            100                 105                 110

Gln Gln His Tyr Thr Thr Pro Pro Thr Phe Gly Gln Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 16
<211> LENGTH: 238
<212> TYPE: PRT
<213> ORGANISM: Artificial Sequence
<220> FEATURE:
<223> OTHER INFORMATION: bH1-P5P7-Fab

<400> SEQUENCE: 16

```
Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Pro His Ser Ile Ser Gly Tyr Val Ala Trp Tyr Gln Gln Lys Pro
    50                  55                  60

Gly Lys Ala Pro Lys Leu Leu Ile Tyr Trp Gly Ser Tyr Leu Tyr Ser
65                  70                  75                  80
```

-continued

Gly Val Pro Ser Arg Phe Ser Gly Ser Gly Thr Asp Phe Thr
                85                  90                  95

Leu Thr Ile Ser Ser Leu Gln Pro Glu Asp Phe Ala Thr Tyr Tyr Cys
            100                 105                 110

Gln Gln His Tyr Thr Thr Pro Pro Thr Phe Gly Gln Gly Thr Lys Val
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 17
<211> LENGTH: 238
<212> TYPE: PRT
<213> ORGANISM: Artificial Sequence
<220> FEATURE:
<223> OTHER INFORMATION: bH1-P5P8-Fab

<400> SEQUENCE: 17

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Pro Arg His Ile Ser Gly Tyr Val Ala Trp Tyr Gln Gln Lys Pro
    50                  55                  60

Gly Lys Ala Pro Lys Leu Leu Ile Tyr Trp Gly Ser Tyr Leu Tyr Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Tyr Cys
            100                 105                 110

Gln Gln His Tyr Thr Thr Pro Pro Thr Phe Gly Gln Gly Thr Lys Val
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

```
Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 18
<211> LENGTH: 468
<212> TYPE: PRT
<213> ORGANISM: Artificial Sequence
<220> FEATURE:
<223> OTHER INFORMATION: bH1-P5-FSA

<400> SEQUENCE: 18

Met Asp Trp Thr Trp Arg Ile Leu Phe Leu Val Ala Ala Ala Thr Gly
1               5                  10                  15

Thr His Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr His Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335
```

```
Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Leu Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
                435                 440                 445

Val Met His Glu Ala Leu His Asn His Tyr Thr Gln Lys Ser Leu Ser
    450                 455                 460

Leu Ser Pro Gly
465
```

```
<210> SEQ ID NO 19
<211> LENGTH: 360
<212> TYPE: DNA
<213> ORGANISM: Artificial Sequence
<220> FEATURE:
<223> OTHER INFORMATION: bH1-P5-Fv

<400> SEQUENCE: 19
gaggtgcagc tggtggagag cggcggcggc ctggtgcagc ccggcggcag cctgagactg      60
agctgcgccg ccagcggctt caacatcaag gacacctaca tccactgggt gagacaggcc     120
cccggcaagg gcctggagtg ggtggccaga atctacccca acggctacac ccactac        180 gccgacagcg tgaagggcag attcaccatc agcgccgaca ccagcaagaa caccgcctac     240
ctgcagatga acagcctgag agccgaggac accgccgtgt actactgcag cagatggggc     300
ggcgacggct ctacgccat ggactactgg ggccagggca ccctggtgac cgtgagcagc      360

<210> SEQ ID NO 20
<211> LENGTH: 333
<212> TYPE: DNA
<213> ORGANISM: Artificial Sequence
<220> FEATURE:
<223> OTHER INFORMATION: bH1-P5-Fv

<400> SEQUENCE: 20
gacatccaga tgacccagag ccccagcagc ctgagcgcca gcgtgggcga cagagtgacc      60
atcacctgca gagccagcca ggacatcccc agaagcatca gcggctacgt ggcctggtac     120
cagcagaagc ccggcaaggc ccccaagctg ctgatctact ggggcagcta cctgtacagc     180
ggcgtgccca gcagattcag cggcagcggc agcggcaccg acttcaccct gaccatcagc     240
agcctgcagc ccgaggactt cgccacctac tactgccagc agcactacac cacccccccc     300
accttcggcc agggcaccaa ggtggagatc aag                                  333

<210> SEQ ID NO 21
<211> LENGTH: 333
<212> TYPE: DNA
<213> ORGANISM: Artificial Sequence
<220> FEATURE:
<223> OTHER INFORMATION: bH1-P5P7-Fv
```

```
<400> SEQUENCE: 21
gacatccaga tgacccagag ccccagcagc ctgagcgcca gcgtgggcga cagagtgacc      60
atcacctgca gagccagcca ggacatcccc cacagcatca gcggctacgt ggcctggtac     120
cagcagaagc ccggcaaggc ccccaagctg ctgatctact ggggcagcta cctgtacagc     180
ggcgtgccca gcagattcag cggcagcggc agcggcaccg acttcaccct gaccatcagc     240
agcctgcagc ccgaggactt cgccacctac tactgccagc agcactacac cacccccccc     300
accttcggcc agggcaccaa ggtggagatc aag                                   333

<210> SEQ ID NO 22
<211> LENGTH: 333
<212> TYPE: DNA
<213> ORGANISM: Artificial Sequence
<220> FEATURE:
<223> OTHER INFORMATION: bH1-P5P8-Fv

<400> SEQUENCE: 22
gacatccaga tgacccagag ccccagcagc ctgagcgcca gcgtgggcga cagagtgacc      60
atcacctgca gagccagcca ggacatcccc agacacatca gcggctacgt ggcctggtac     120
cagcagaagc ccggcaaggc ccccaagctg ctgatctact ggggcagcta cctgtacagc     180
ggcgtgccca gcagattcag cggcagcggc agcggcaccg acttcaccct gaccatcagc     240
agcctgcagc ccgaggactt cgccacctac tactgccagc agcactacac cacccccccc     300
accttcggcc agggcaccaa ggtggagatc aag                                   333
```

ANTIBODY VARIANTS WITH pH-DEPENDENT ANTIGEN BINDING FOR SELECTIVE TARGETING OF SOLID TUMORS

RELATED APPLICATIONS

This application is a national stage filing under 35 U.S.C. § 371 of International Patent Application Serial No. PCT/IB2020/053024, filed Mar. 30, 2020, which claims priority under 35 U.S.C. § 119(e) of U.S. Application Ser. No. 62/828,024, filed Apr. 2, 2019, the entire contents of each of which are incorporated herein by reference in its entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on May 16, 2022, is A089970018US00-SUB-SEQ-LJG and is 21,709 bytes in size.

FIELD OF THE INVENTION

The technology consists of antibody variants and fragments thereof capable of binding to the human tumor target Her2 in a pH-dependent manner, and uses thereof. More specifically, the present invention relates to Her2 binding molecules with reduced affinities to normal cells or tissues at physiological pH relative to their affinities to tumor cells and tissues under slightly acidic pH, which can lead to high safety and low toxicity for therapeutic or diagnostic uses in humans.

BACKGROUND OF THE INVENTION

Antibody-based anti-cancer therapeutics are intended to target antigens present on tumor cells. Specific tumor targeting can be accomplished on those antigens exclusively found on cancer cells and not present at all on normal cells, like a splice variant of EGFR (EGFRvIII) specific to glioma cells for example [1]. In most cases, however, the target antigen overexpressed by cancer cells is also present at lower concentration in normal tissues. In order to reduce antibody toxicity in these cases, one strategy is to take advantage of the higher antigen density on tumor cells relative to normal cells [2-5][WO2012075581; WO2012100346]. This approach requires modulation of antibody-antigen affinity, e.g., by mutagenesis of the complementarity determining region (CDR), to an optimal range where binding to the low-density antigen on normal cells is reduced while a reasonable level of binding to the high-density antigen present on tumor cells is retained. This results from the avidity of bridged binding that can be achieved by typical bivalent antibodies and related constructs. The optimal range of monovalent binding selectivity is found empirically and is system dependent; too little or too much affinity weakening can lead to maintained binding at low-density, or loss of binding at high-density, respectively. The avidity-based approach can only be applied when there is a significant antigen overexpression on tumor cells and their surrounding stroma.

A completely different optimization strategy for specific tumor targeting is proposed herein, which exploits the slightly higher acidity of the tumor relative to normal tissues pH [6, 7]. Due to several factors including poor vascular perfusion, regional hypoxia, and fermentative glycolysis,[8] the pH surrounding solid tumor cells is in the 6.0-6.8 range [9-14], whereas the pH surrounding normal cells is at physiological levels (7.2-7.4). In order to take advantage of this differential pH for reducing antibody toxicity on normal cells, CDR mutagenesis can be aimed at introducing a certain level of pH dependence into the antibody binding affinity to the antigen, such that binding is significantly weakened at physiological pH relative to the acidic pH. Since the ionization constant of the histidine on the protein surface is ~6.4 [15], histidine scanning mutagenesis is applied in this type of design.

De novo engineering of pH-dependent antibody binding had overwhelmingly focused towards weakening binding at acidic pH relative to the physiological pH. When antibody CDRs were mutated in order to generate so-called recycling or sweeping antibodies, the motivation was mainly to direct overexpressed antigens to lysosomal degradation following dissociation in the acidic endosomes from their antibody complexes [16-24]. A similar approach was also employed to engineer pH dependent dissociation into antibody sequences outside of the CDR or into non-antibody protein-protein complexes [25-27]. From a completely different perspective, protein domains were engineered against non-CDR antibody surfaces as binding reagents at neutral pH from which antibodies can be eluted at acidic pH [28-31]. Engineered selectivity towards the acidic pH was rarely reported, aimed at extending half-lives in blood. Examples include de novo engineering of an affibody protein for binding to the recycling neonatal receptor (FcRn) at the acidic pH of early endosomes [32], and modulating the already present pH-dependent binding of Fc to FcRn to further improve binding selectivity towards acidic pH [33].

Expectedly, histidine mutagenesis has been the workhorse for most of these pH-dependent binding engineering efforts, either by screening of recombinant variants or selection from combinatorial display libraries. While computational design has been successfully applied to antibody-antigen affinity maturation [34, 35], successfully predicting pH-dependent antigen-binding CDRs of antibodies has been limited thus far. To our knowledge, only two previous computational structure-based design studies reported successful prospective engineering of pH-dependent binding proteins, both aimed at weakening binding at acidic pH [25, 30]. A computational framework for structure-based design of pH-dependent binding was also proposed and used to retrospectively recapitulate previous Fc-FcRn pH-dependent binding data [36].

In this study, the anti-Her2 Fab called bH1 was selected as starting point for structure-based de novo engineering of pH-dependent antigen binding. In addition to its available crystal structure in complex with the antigen, bH1 binds Her2 with reduced affinity relative to the related antibody Herceptin [37][WO2008027236; WO2010027981; WO2010108127; WO2015095539]. As mentioned earlier, this is a desired characteristic that can be used to reduce toxicity to normal cells via avidity. Here, we first implemented dual-pH histidine-scanning mutagenesis into the Assisted Design of Antibody and Protein Therapeutics (ADAPT) platform previously used for antibody-antigen affinity maturation at physiological pH [35, 38]. The extended computational platform was then applied to the structure of the bH1-Her2 complex aiming at improved binding selectivity towards acidic pH versus normal pH. Rational designs were first tested as Fabs at two pHs, for in vitro binding to the soluble recombinant Her2 ectodomain and then for binding to intact Her2 expressed at cell surface.

Full-size antibody (FSA) versions of successfully designed mutants were then tested on Her2 expressing cells as a function of pH within the 5.2-7.3 range. Rationally designed FSA variants displayed marked selectivity towards the extracellular pH of solid tumors versus normal tissues.

SUMMARY OF THE INVENTION

Recent development of monoclonal antibodies as mainstream anticancer agents demands further optimization of their safety for use in humans. Potent targeting and/or effector activities on normal tissues is an obvious toxicity concern. Optimization of specific tumor targeting could be achieved by taking advantage of the extracellular acidity of the solid tumors relative to normal tissues. Here, a structure-based computational approach was applied to engineer anti-Her2 antibodies with selective binding in the acidic tumor microenvironment. We used an affinity maturation platform in which dual-pH histidine-scanning mutagenesis was implemented for pH selectivity optimization. Testing of a small set of designs for binding to the recombinant Her2 ectodomain led to the identification of Fab variants with the desired pH-dependent binding behavior. Binding selectivity towards acidic pH was improved by as much as 25-fold relative to the parental bH1-Fab. In vitro experiments on cells expressing intact Her2 confirmed that designed variants formatted as IgG1/k full-size antibodies have high affinity and inhibit the growth of tumor spheroids at a level comparable to that of the benchmark anti-Her2 antibody Herceptin at acidic pH, whereas these effects were significantly reduced at physiological pH. In contrast, both Herceptin and the parental bH1 antibody exhibited strong cell binding and growth inhibition irrespective of pH. These acidic pH-selective variants are usefully and advantageous alternatives for tumour targeting antibodies and for development of novel CAR-T cells, bispecifics and ADCs with reduced toxicities.

The present invention provides an anti-Her2 antibody, antibody fragment, or antigen-binding fragment thereof comprising complementarity determining region (CDR)-H1 comprising sequence GFNIKDTYIH (SEQ ID NO:1), CDR-H2 comprising sequence RIYPTNGYTHYADSVKG (SEQ ID NO:2), CDR-H3 comprising sequence WGGDGFYAMDY (SEQ ID NO: 3), CDR-L1 comprising sequence RASQDIPX$_1$X$_2$ISGYVA (SEQ ID NO:4), CDR-L2 comprising sequence WGSYLYS (SEQ ID NO:5) and CDR-L3 comprising sequence QQHYTTPPT (SEQ ID NO:6) or a sequence substantially identical thereto; wherein: X$_1$ is R or H, and X$_2$ is S or H. In preferred embodiments, SEQ ID NO: 4 may comprise a sequence selected from the group consisting of SEQ ID NO:7, SEQ ID NO:8 and SEQ ID NO:9, or any sequence substantially identical thereto.

The provided antibody, antibody fragment or antigen-binding fragment thereof may comprise a heavy-chain variable sequence comprising SEQ ID NO:10; and a light-chain variable sequence comprising a sequence selected from the group consisting of SEQ ID NO:11, SEQ ID NO:12 and SEQ ID NO:13; or a sequence substantially identical thereto.

The provided antibody, antibody fragment, or antigen-binding fragment thereof of the present invention preferentially and selectively bind to Her2 or Her2-expressing cells with increased binding at an acidic pH (pH between 5.0-6.8) relative to a physiological pH (pH between 7.2-7.4). The provided antibody, antibody fragment or antigen-binding fragment may bind Her2 or Her2-expressing cells with an at least 10-fold increase in binding affinity at an acidic pH relative to a physiological pH. The antibodies now provided preferentially bind to Her2 or Her2-expressing cells in a slightly acidic pH (pH 5.0 to 6.8), and dissociate from Her2 or Her2-expressing cells when pH is increased (pH above 7.2). The at least 10-fold increase in binding affinity is defined as a ratio of apparent equilibrium dissociation constants, with selectivity towards the slightly acidic pH conditions relative to physiological pH conditions. For example, the provided antibody may bind to Her2-expressing cells with an apparent $K_D$ of less than 50 nM in an acidic environment. In accordance with the present invention, the term "acidic pH" may be any pH value between 5.0-6.8 (for example, a pH of 5.0, 5.7, 6.4, 6.5, 6.8 or any pH within said range); whereas a "physiological pH" means any pH value between 7.2-7.4.

The provided antibody, antibody fragment, or antigen-binding fragment thereof of the present invention preferentially and selectively inhibits growth of Her2-expressing cells at an acidic pH (for example at pH 6.4) relative to a physiological pH (for example at pH 7.4).

The provided antibody, antibody fragment, or antigen-binding fragment thereof of the present invention preferentially and selectively internalizes into Her2-expressing cells at an acidic pH (for example at pH 6.4) relative to a physiological pH (for example at pH 7.4).

The provided antibody, antibody fragment, or antigen-binding may be full size antibody (FSA), bivalent full-size antibody, Fab fragment thereof, or any antibody fragment comprising CDR-H1 comprising sequence GFNIKDTYIH (SEQ ID NO:1), CDR-H2 comprising sequence RIYPTNGYTHYADSVKG (SEQ ID NO:2), CDR-H3 comprising sequence WGGDGFYAMDY (SEQ ID NO: 3), CDR-L1 comprising sequence RASQDIPX$_1$X$_2$ISGYVA (SEQ ID NO:4), CDR-L2 comprising sequence WGSYLYS (SEQ ID NO:5) and CDR-L3 comprising sequence QQHYTTPPT (SEQ ID NO:6) or a sequence substantially identical thereto; wherein: X$_1$ is R or H, and X$_2$ is S or H. For example, the provided antibody, antibody fragment or antigen-binding fragment may comprise a format that is a scFv, di-scFv, Fab, Fab', F(ab')$_2$, a multimer thereof, a bi-specific T-cell engager (BiTE), or a bi/tri/multi-specific killer cell engager.

The provided antibody, antibody fragment or antigen-binding fragment may comprise a constant region of human origin.

The provided antibody, antibody fragment or antigen-binding fragment may comprise a sequence selected from the group consisting of SEQ ID NO:14, SEQ ID NO:15, SEQ ID NO:16, SEQ ID NO:17 and SEQ ID NO:18; or a sequence substantially identical thereto.

The provided antibody, antibody fragment or antigen-binding fragment may be comprised in a protein fusion. One of skill in the present art would understand that said fusion proteins may comprise, but is not limited to, one or more than one components including a linker sequences (such as any linker sequence that would allow for the operable fusion of antibody domains to form an antibody or antigen-binding fragment thereof), targeting or signal sequences, a detection/purification tag or any additional sequence, or a combination thereof.

The provided antibody, antibody fragment or antigen-binding fragment may be comprised in a chimeric antigen receptor (CAR). The CAR may further comprise a spacer, a transmembrane domain, and may optionally include at least one costimulatory domain (for example, CD28) or at least one intracellular signalling domain (for example, CD3 zeta).

The provided antibody, antibody fragment or antigen-binding fragment may be in a multivalent or multispecific display format.

There are also provided nucleic acid molecules or vectors encoding any of the provided antibody, antibody fragment or antigen-binding fragments thereof or any of the fusion proteins comprising said antibodies, antibody fragments or antigen-binding fragments.

The provided antibody, antibody fragment or antigen-binding fragment thereof may be immobilized onto a surface, for example, but not limited to, a solid surface.

The provided antibody, antibody fragment or antigen-binding fragment thereof may be linked to a cargo molecule. The cargo molecule may be a detectable agent, a therapeutic, a drug, a peptide, a carbohydrate moiety, an enzyme, or a cytotoxic agent; one or more liposomes loaded with a detectable agent, a therapeutic, a drug, a peptide, an enzyme, or a cytotoxic agent; or one or more nanoparticle, nanowire, nanotube, or quantum dots.

The antibodies or fragments thereof of the present invention, linked to a cargo molecule such as a cytotoxic drug, preferentially inhibit growth of Her2-expressing cells selectively at an acidic pH (for example at pH 6.4) relative to a physiological pH (for example pH 7.4).

The present invention provides a composition, for example a pharmaceutical composition comprising one or more than one antibody, antibody fragment or antigen-binding fragment thereof wherein said composition may additionally comprise a pharmaceutically-acceptable carrier, diluent, or excipient.

The present invention provides a cell comprising or expressing the provided antibody, antibody fragment or antigen-binding fragment. The provided cell may comprise a nucleic acid or vector encoding any of the provided antibody, antibody fragment or antigen-binding fragments. The present invention provides a kit comprising any cell expressing, any nucleic acid sequence or vector encoding, or any composition comprising any antibody, antibody fragment or antigen-binding fragment of the present invention.

The present invention provides a method of treating solid tumors, or any Her2-producing tumours comprising the use or administration of any antibody, antibody fragment or antigen-binding fragment of the present invention, to a subject in need thereof.

The present invention also provides a method of detecting solid tumors, or any Her2-producing tumours in a subject, comprising the use or administration of any antibody, antibody fragment or antigen-binding fragment of the present invention, or any composition comprising the same, in a subject, and detecting the bound antibody, antibody fragment or antigen-binding fragment using a suitable detection and/or imaging technology.

The present invention also provides a method of capturing the Her2 ectodomain, comprising contacting a sample with one, or more than one, antibody, antibody fragment or antigen-binding fragment of the present invention, and allowing the Her2 ectodomain to bind to the antibody or fragment thereof in slightly acidic pH (pH between 5.0 and 6.8), and releasing the Her2 ectodomain from the antibody or fragment thereof by raising the pH to 7.2-7.4.

The present invention confirms and provides a method comprising a rational structure-guided affinity optimization of a parent anti-tumour antibody to modulate binding selectivity at varying pH levels, in this case the weakened binding of an anti-Her2 antibody in the physiological environment relative to the parent, while maintaining the strong binding affinity ($K_D$<50 nM) in the acidic environment. The pH sensitivity now provided to the novel anti-Her2 variants in the present invention advantageously allow for the modulation of binding relative to the pH environment. This is highly favourable for immunotherapeutics targeting cancerous tumour cells, for example but not limited to breast cancer cells.

The present invention relates to antibody variants and fragments thereof capable of binding to the human tumor target Her2 in a pH-dependent manner, and uses thereof. More specifically, the present invention relates to Her2 binding molecules with reduced affinities to normal cells or tissues at physiological pH relative to their affinities to tumor cells and tissues under slightly acidic pH, which can lead to high safety and low toxicity for therapeutic or diagnostic uses in humans.

The present invention provides an antibody or fragment thereof comprising a sequence of: CDR-H1 of GFNIKDTYIH (SEQ ID NO:1), CDR-H2 of RIYPTNGYTHYADSVKG (SEQ ID NO:2), CDR-H3 of WGGDGFYAMDY (SEQ ID NO: 3), CDR-L1 of RASQDIPX$_1$X$_2$ISGYVA (SEQ ID NO:4), CDR-L2 of WGSYLYS (SEQ ID NO:5) and CDR-L3 of QQHYTTPPT (SEQ ID NO:6); wherein: X$_1$ is R or H, and X$_2$ is S or H (SEQ ID NO:7, SEQ ID NO:8, SEQ ID NO:9).

The present invention provides an antibody, antibody fragment or antigen binding fragment that specifically binds Her2 with an increased binding affinity of at least 10-fold in a pH range of 5.0-6.8 relative to a physiological pH (i.e. pH of 7.2-7.4). The provided anti-Her2 binding antibody may be a full-size antibody, an antibody fragment or an antigen binding fragment comprising CDR-H1, -H2, -H3, -L1, -L2 and -L3 having sequences SEQ ID NO: 1, 2, 3, 4, 5 and 6 respectively, or any sequence substantially identical thereto.

The present invention also provides an antibody or fragment thereof that may be selected from the group consisting of a heavy-chain variable sequence of SEQ ID NO:10; and the light-chain variable sequence selected from the group consisting of SEQ ID NO:11, SEQ ID NO:12 and SEQ ID NO:13; or a sequence substantially identical thereto.

The antibodies or fragments thereof provided by the present invention bind to Her2-expressing cells selectively in slightly acidic conditions (e.g., pH in the 5.0-6.8 range) relative to the physiological pH environment (pH of 7.2-7.4). In certain embodiments, the full-size antibodies and their corresponding Fab fragments bind to Her2-expressing cells with at least 10-fold weaker apparent affinity at pH 7.3 than in slightly acidic conditions.

The antibodies or fragments thereof provided by the present invention inhibits growth of Her2-expressing cells selectively in slightly acidic conditions (for example at pH 6.4) relative to the physiological pH environment (for example pH at 7.4).

The antibodies or fragments thereof provided by the present invention internalize into Her2-expressing cells selectively in slightly acidic conditions (for example at pH 6.4) relative to the physiological pH environment (for example pH at 7.4).

In certain embodiments, the antibodies or fragments thereof comprise a constant region of human origin. Hence, these antibodies or fragments thereof are selected from the group consisting of SEQ ID NO:14, SEQ ID NO:15, SEQ ID NO:16, SEQ ID NO:17 and SEQ ID NO:18; or a sequence substantially identical thereto.

In other embodiments, the antibody fragments can be in the scFv (single-chain variable domain) format, in a di-scFv, Fab, F(ab) multimer, or a BITE® (bi-specific T-cell engager). In yet other embodiments, the antibodies or fragments thereof are protein fusions, for example, in a CAR (chimeric antigen receptor) format displayed on cell surface, or in a multivalent display format, or in a multispecific display format.

The antibodies and antibody fragments of the present invention may be produced recombinantly. The present invention further encompasses nucleic acid molecules encoding the antibodies or fragments thereof as described above. The present invention also includes vectors comprising said nucleic acid molecules.

The antibodies or fragments thereof as described herein may be immobilized onto a surface.

The antibodies or fragments thereof of the present invention may be linked to a cargo molecule; the cargo molecule may be a detectable agent, a therapeutic, a drug, a peptide, a carbohydrate moiety, an enzyme, or a cytotoxic agent; one or more liposomes loaded with a detectable agent, a therapeutic, a drug, a peptide, an enzyme, or a cytotoxic agent; or one or more nanoparticle, nanowire, nanotube, or quantum dots.

The antibodies or fragments thereof of the present invention linked to a cargo molecule such as a cytotoxic drug inhibit growth of Her2-expressing cells selectively in slightly acidic conditions (for example at pH 6.4) relative to the physiological pH environment (for example at pH 7.4).

Also provided is a composition comprising one or more than one antibody or fragment thereof of the present invention and a pharmaceutically-acceptable carrier, diluent, or excipient.

The present invention further provides a method of selectively targeting Her2-expressing cancer cells and tumor tissues, and treating solid tumors with minimal unwanted off-tumor host toxicity and a wide therapeutic window, comprising administering the antibodies or fragments thereof of the present invention or the composition described above to a subject in need thereof.

The present invention also provides a method of detecting solid tumors, comprising administering the antibodies or fragments thereof of the present invention or the composition described above, and detecting the bound antibody or fragment thereof using a suitable detection and/or imaging technology.

The present invention further provides a method of capturing the Her2 ectodomain, comprising contacting a sample with one or more than one surface-immobilized antibodies or fragments thereof of the present invention, and allowing the Her2 ectodomain to bind to the antibodies or fragments thereof in slightly acidic pH conditions, e.g., pH between 5.0 and 6.8, and releasing the Her2 ectodomain from the antibody or fragment thereof by raising the pH to 7.2-7.4.

Additional aspects and advantages of the present invention will be apparent in view of the following description. The detailed description and examples, while indicating preferred embodiments of the invention, are given by way of illustration only, as various changes and modifications within the scope of the invention will become apparent to those skilled in the art in light of the teachings of this invention.

BRIEF DESCRIPTION OF THE DRAWINGS

These and other features of the invention will now be described by way of example, with reference to the appended drawings, wherein:

(FIG. 6A) High-density Her2 cells (SKOV3) were tested in environments with varying pH between 5.2 and 7.3 and cell binding was analyzed by fluorescence-activated cell sorting (FACS) at varying concentrations of the FSA variants. (FIG. 6B) Apparent dissociation constants ($K_D$) of tested FSA variants from binding experiments to high-density Her2 cells (SKOV3) at various pHs.

DETAILED DESCRIPTION OF THE INVENTION

Figure 1:
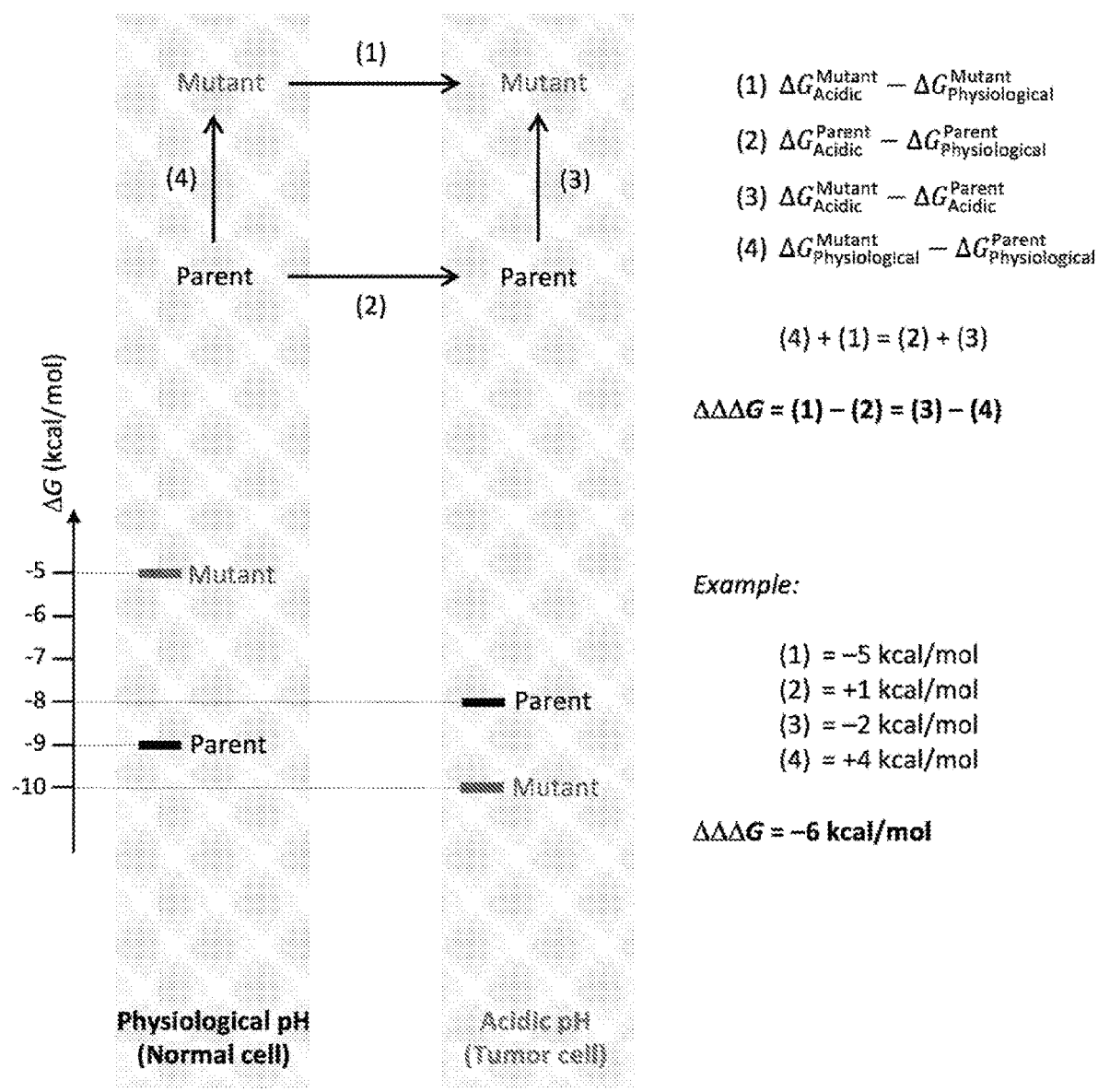
FIG. 1. Definition of relative binding free energy function for computational optimization of pH dependence. The main property to be optimized is $\Delta\Delta\Delta G_{binding}$, the binding free energy gap between the Acidic and Physiological environments of a Mutant relative to the Parent, which has to be as negative as possible. This is shown in the upper diagram as the difference given by (1)-(2). Computationally, we simulate (3)-(4) instead, which from the thermodynamic cycle yields the same quantity. The bottom diagram provides an illustrative example for a possible distribution of free energies for the 4 states shown in the thermodynamic cycle, and how $\Delta\Delta\Delta G_{binding}$ can be calculated based on these free energies.

The present invention relates to anti-Her2 antibodies and uses thereof. More specifically, the present invention relates to anti-Her2 antibodies and fragments thereof with preferential binding to cancer cells in slightly acidic environment relative to normal cells at physiological pH environment.

The present invention provides engineered recombinant full-size antibodies (FSAs) and fragments thereof capable of binding selectively to Her2 expressing cells at slightly acidic pH in the 5.0-6.8 range relative to the physiological pH of 7.2-7.4. Without wishing to be bound by theory, the environment surrounding solid tumors is slightly acidic relative to normal cells. Achieving pH dependent binding selectivity towards acidic pH with reduced binding at physiological pH of normal cells represents a novel means of reducing off-tumor host toxicities of antibody-based therapeutics and widening their therapeutic windows.

The use of the terms "a" and "an" and "the" and similar referents in the context of describing the invention (especially in the context of the claims) are to be construed to cover both the singular and the plural, unless otherwise indicated herein or clearly contradicted by context.

Unless specifically stated or obvious from context, as used herein the term "or" is understood to be inclusive and covers both "or" and "and". The term "and/or" where used herein is to be taken as specific disclosure of each of the specified features or components with or without the other.

The terms "comprising", "having", "including", and "containing" are to be construed as open-ended terms (i.e., meaning "including, but not limited to") unless otherwise noted. The term "consisting of" is to be construed as close-ended. The term "consisting essentially of" when used in the context of CDR sequences means that the CDR sequence may be slightly (e.g., +/−1 or 2 aa) longer or shorter.

The term "antibody", also referred to in the art as "immunoglobulin" (Ig), used herein refers to a protein constructed from paired heavy and light polypeptide chains; various Ig isotypes exist, including IgA, IgD, IgE, IgG, and IgM. When an antibody is correctly folded, each chain folds into a number of distinct globular domains joined by more linear polypeptide sequences. For example, the immunoglobulin light chain folds into a variable ($V_L$) and a constant ($C_L$) domain, while the heavy chain folds into a variable ($V_H$) and three constant ($C_{H1}$, $C_{H2}$ and $C_{H3}$) domains. Interaction of the heavy and light chain variable domains ($V_H$ and $V_L$) results in the formation of an antigen binding region (Fv). Each domain has a well-established structure familiar to those of skill in the art. An antibody may be, but is not limited to, full length antibodies, an antigen binding fragment comprising a $V_L$ and $V_H$ domain, such as Fab, Fv, scFv, dsFv, BiTE, or any multimer of said antigen binding fragment.

The light and heavy chain variable regions are responsible for binding the target antigen and can therefore show significant sequence diversity between antibodies. The constant regions show less sequence diversity, and are responsible for binding a number of natural proteins to elicit important biochemical events. The variable region of an antibody contains the antigen binding determinants of the molecule, and thus determines the specificity of an antibody for its target antigen. The majority of sequence variability occurs in six hypervariable regions, three each per variable heavy ($V_H$) and light ($V_L$) chain; the hypervariable regions combine to form the antigen-binding site, and contribute to binding and recognition of an antigenic determinant. The specificity and affinity of an antibody for its antigen is determined by the structure of the hypervariable regions, as well as their size, shape and chemistry of the surface they present to the antigen. Various schemes exist for identification of the regions of hypervariability, the two most common being those of Kabat and of Chothia. Kabat et al. define the "complementarity-determining regions" (CDR) based on sequence variability at the antigen-binding regions of the $V_H$ and $V_L$ domains [39]. Chothia and Lesk define the "hypervariable loops" (H or L) based on the location of the structural loop regions in the $V_H$ and $V_L$ domains [40]. As these individual schemes define CDR and hypervariable loop regions that are adjacent or overlapping, those of skill in the antibody art often utilize the terms "CDR" and "hypervariable loop" interchangeably, and they may be so used herein. For this reason, the regions forming the antigen-binding site are presently referred to herein as CDR-L1, CDR-L2, CDR-L3, CDR-H1, CDR-H2 and CDR-H3, and they follow the Kabat definition, except for CDR-H1 that is taken here as the union of the Kabat and Chothia definitions. The CDR/loops can also be referred to according to the IMGT numbering system [41], which was developed to facilitate comparison of variable domains. Additionally, standardized delimitations of the framework regions of the $V_H$ and $V_L$ domains outside of the CDR can be formulated according to each CDR definition scheme.

An "antibody fragment" as referred to herein may include any suitable antigen-binding antibody fragment known in the art. The antibody fragment may be a naturally-occurring antibody fragment, or may be obtained by manipulation of a naturally-occurring antibody or by using recombinant methods. For example, an antibody fragment may include, but is not limited to a Fv, a single-chain Fv (scFv; a molecule consisting of $V_L$ and $V_H$ connected with a peptide linker), a Fab, a single-chain Fab (scFab; a molecule consisting of $V_L$ and $C_H$ connected with a peptide linker, or of $V_H$ and $C_L$ connected with a peptide linker), F(ab')$_2$, and multivalent presentations of any of these. For example, multiple Fv fragments can be linked, or multiple Fab fragments can be linked, via the heavy chain, or light chain, or both. Non-limiting examples of antibody fragments and possible multivalent assemblies are known in the art [42-44]. As used herein the term "antigen-binding domain" or "antigen-binding fragment" refers to the domain of an antibody or of an antigen-binding fragment which allows binding to an antigen.

Thus, present invention provides an antibody or fragment thereof comprising a sequence of: CDR-H1 of GFNIKDTYIH (SEQ ID NO:1), CDR-H2 of RIYPTNGYTHYADSVKG (SEQ ID NO:2), CDR-H3 of WGGDGFYAMDY (SEQ ID NO: 3), CDR-L1 of RASQDIPX$_1$X$_2$ISGYVA (SEQ ID NO:4), CDR-L2 of WGSYLYS (SEQ ID NO:5) and CDR-L3 of QQHYTTPPT (SEQ ID NO:6); wherein: X$_1$ is R or H, and X$_2$ is S or H (SEQ ID NO:7, SEQ ID NO:8, SEQ ID NO:9).

As would be understood by those of skill in the art, not all CDR may be required for binding the antigen. For example, and without wishing to be limiting, one, two, three, four, five or all six CDR loops may contribute to binding and recognition of the antigen by the sdAb of the present invention.

In a non-limiting example, the antibody or fragment is recombinantly produced and includes modifications engineered by site-directed mutagenesis and affinity modulation of a parental antibody. Encompassed by the present invention are any homologues, derivatives, or fragments of the antibodies and fragments thereof disclosed here that retain the pH-dependent binding selectivity to Her2 of the antibodies and fragments thereof disclosed here.

As previously stated, the antibody or fragment may be recombinantly produced and thus may be based on chosen framework regions; alternatively, the CDR described above may be grafted onto other $V_H$ or $V_L$ framework regions. In yet another alternative, the hypervariable loops described above may be grafted onto the framework regions of other types of antibody fragments (e.g., Fv, scFv, Fab, scFab, and their combination and multivalent formats). The present embodiment further encompasses an antibody or an antibody fragment whereby the CDR is grafted into framework regions chosen from various species.

In a specific, non-limiting example, the antibody or fragment thereof that is selective for Her2 binding at acidic pH comprise a sequence selected from the group consisting of a heavy-chain variable sequence of SEQ ID NO:10; and the light-chain variable sequence selected from the group consisting of SEQ ID NO:11, SEQ ID NO:12 and SEQ ID NO:13; or a sequence substantially identical thereto.

In certain embodiments, the antibodies or fragments thereof comprise a constant region of human origin. Hence, in specific non-limiting examples, antibodies or fragments thereof are selected from the group consisting of SEQ ID NO:14, SEQ ID NO:15, SEQ ID NO:16, SEQ ID NO:17 and SEQ ID NO:18; or a sequence substantially identical thereto.

A "substantially identical" sequence may comprise one or more conservative amino acid mutations. It is known in the art that one or more conservative amino acid mutations to a reference sequence may yield a mutant peptide with no substantial change in physiological, chemical, physico-chemical or functional properties compared to the reference sequence; in such a case, the reference and mutant sequences would be considered "substantially identical" polypeptides. Conservative amino acid mutation may include addition, deletion, or substitution of an amino acid; a conservative amino acid substitution is defined herein as the substitution of an amino acid residue for another amino acid residue with similar chemical properties (e.g. size, charge, or polarity).

In a non-limiting example, a conservative mutation may be an amino acid substitution. Such a conservative amino acid substitution may substitute a basic, neutral, hydrophobic, or acidic amino acid for another of the same group. By the term "basic amino acid" it is meant hydrophilic amino acids having a side chain pKa value of greater than 7, which are typically positively charged at physiological pH. Basic amino acids include arginine (Arg or R) and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of [45]. Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pKa value of less than 7, which are typically negatively charged at physiological pH. Acidic amino acids include glutamate (Glu or E), and aspartate (Asp or D). Histidine (His or H) is a polar amino acid with a special ionization potential due to its pKa around 7, and more precisely around 6.4 in case of histidine residues located at the protein surface [15].

This results in histidine amino acid residues being a "polar" and predominantly uncharged at physiological pH of 7.2-7.4, and predominantly positively charged in acidic environments (pH<7).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2 service maintained by the Swiss Institute of Bioinformatics (and as found at http://ca.expasy.org/tools/blast/), BLAST-P, Blast-N, or FASTA-N, or any other appropriate software that is known in the art.

The substantially identical sequences of the present invention may be at least 65% identical; in another example, the substantially identical sequences may be at least 65, 70, 85, 90, 95, 96, 97, 98, 99, or 100% identical, or any percentage there between, at the amino acid level to sequences described herein. Importantly, the substantially identical sequences retain the activity and specificity of the reference sequence. In a non-limiting embodiment, the difference in sequence identity may be due to conservative amino acid mutation(s). By way of example only, and without wishing to be limiting in any manner, the bH1 Fab fragment used as parental antibody in this invention and the Fab fragment of the anti-Her2 antibody Herceptin share the same heavy chain (100% identity) and have a light chain variable domains ($V_L$) that differ at 11 positions, which is equivalent to 95.3% sequence identity in the combined variable domains. By way of other examples, and without wishing to be limiting in any manner, affinity modulated and affinity matured Herceptin variants have been described which differ only by 1 to 3 amino-acids, equivalent to 98.9-99.6% sequence identity, in the combined variable domains [35, 46][WO2012075581], as well as affinity modulated and affinity matured bH1 variants that differ by 1 to 12 amino acids, equivalent to 94.2-99.6% sequence identity, in the combined variable domains [35, 37, 47]. Hence, the present invention also encompasses histidine mutated variants of Herceptin, as well as of aforementioned Herceptin and bH1 affinity modulated and affinity matured variants, which contain the same mutation(s) to histidine as the one(s) exemplified here for the parental bH1 sequence which lead(s) to pH-dependent binding selectivity towards the slightly acidic pH relative to physiological pH.

The antibody or fragment thereof of the present invention may also comprise additional sequences to aid in expression, detection or purification of a recombinant antibody or fragment thereof. Any such sequences or tags known to those of skill in the art may be used. For example, and without wishing to be limiting, the antibody or fragment thereof may comprise a targeting or signal sequence (for example, but not limited to ompA), a detection/purification tag (for example, but not limited to c-Myc or a $His_5$ or $His_6$), a linker sequence (wherein one of skill in the present art could use any suitable linker to allow for the operably biological function and association of the antibody domains that form the antigen-binding region; for example, a linker may be $(GGGS)_n$, any multiple thereof, or any suitable linker in the art), or a combination thereof. In another example, the additional sequence may be a biotin recognition site such as that described in WO1995004069 or WO2004076670. As is also known to those of skill in the art, linker sequences may be used in conjunction with the additional sequences or tags, or may serve as a detection/purification tag.

In yet other embodiments, the antibodies or fragments thereof are protein fusions, for example, in a CAR (chimeric antigen receptor) format displayed on cell surface, or in a multivalent display format, or in a multispecific display format.

By way of example only, and without wishing to be limiting in any manner, the antibodies and fragments thereof of the present invention can be reformatting as single-chain variable domains (scFv) for generation of chimeric antigen receptors (CARs) [48]. To this end, the pH-dependent anti-Her2 antibodies and fragments thereof of the present invention have to be formatted as scFv and then fused to a spacer polypeptide, a transmembrane domain (e.g., from CD28) and an endodomain (e.g., CD3-zeta) capable of transmitting an activation signal to the T-cell after the engagement of the Her2 antigen. The 2D-tethering of CARs on the T-cell membrane may also complement their pH-dependent binding with avidity selectivity towards tumor cells.

The antibody or fragment thereof of the present invention may also be in a multivalent display format, also referred to herein as multivalent presentation. Multimerization may be achieved by any suitable method of known in the art. Multimerization may result in homomeric or heteromeric constructs. Homo-multimers can be used for introducing avidity effects, which can improve efficacy and reduce toxicity. For example, and without wishing to be limiting in any manner, homo-multimerization may be achieved using self-assembly molecules as described in [49] and WO2003046560. The described method produces pentabodies by expressing a fusion protein comprising the antibody or fragment thereof of the present invention and the pentamerization domain of the B-subunit of an $AB_5$ toxin family [50]; the pentamerization domain assembles into a pentamer, through which a multivalent display of the antibody or fragment thereof is formed. Each subunit of the pentamer may be the same or different, and may have the same or different specificity. Additionally, the pentamerization domain may be linked to the antibody or antibody fragment using a linker; such a linker should be of sufficient length and appropriate composition to provide flexible attachment of the two molecules, but should not hamper the antigen-binding properties of the antibody. Hetero-multimers can be used for generated multi-specific molecules. Bispecific and multispecific fusion proteins consisting of antibodies and antibody fragments are well known in the art. For example, and without wishing to be limiting, the antibody or fragment thereof may be presented as a dimer, a trimer, or any other suitable oligomer. This may be achieved by methods known in the art, for example direct linking connection, c-jun/Fos interaction [51], "knob into holes" interaction [52], and many other formats known in the art, some of which may employ carefully designed Fc domains [42]. Furthermore, enhanced in vivo efficacy of fragments lacking an Fc domain may be obtained using various techniques, including PEGylation, fusion to serum albumin, or fusion to serum albumin-specific antibody fragments; these approaches increase their blood circulation half-lives, size and avidity.

The antibodies and antibody fragments of the present invention may be produced recombinantly. The present invention further encompasses nucleic acid molecules encoding the antibodies or fragments thereof as described above. The nucleic acid sequence may be codon-optimized for expression in various micro-organisms. The present invention also includes vectors comprising the nucleic acid molecules just described. Furthermore, the invention encompasses cells comprising the nucleic acid and/or vector as described.

The present invention further encompasses the antibodies or fragments thereof immobilized onto a surface using various methodologies. For example, and without wishing to be limiting, the antibody or fragment may be linked or coupled to the surface via His-tag coupling, biotin binding, covalent binding, adsorption, and the like. Immobilization of the antibody or fragment thereof of the present invention may be useful in various applications for capturing, purifying or isolating proteins. The solid surface may be any suitable surface, for example, but not limited to the well surface of a microtiter plate, channels of surface plasmon resonance (SPR) sensorchips, membranes, beads (such as magnetic-based or sepharose-based beads or other chromatography resin), glass, plastic, stainless steel, a film, or any other useful surface such as nanoparticles, nanowires and cantilever surfaces.

The present invention further provides a method of capturing the Her2 ectodomain, comprising contacting a sample with one or more than one surface-immobilized antibodies or fragments thereof of the present invention, and allowing the Her2 ectodomain to bind to the antibodies or fragments thereof in slightly acidic pH conditions, e.g., pH between 5.0 and 6.8, and releasing the Her2 ectodomain from the antibody or fragment thereof by raising the pH to 7.2-7.4. Thus, the antibodies or fragments thereof of the present invention may provide useful affinity purification reagents for preparations of Her2 ectodomain samples.

The antibodies or fragments thereof of the present invention may be linked to a cargo molecule. The cargo molecule may be any suitable molecule. For example, and without wishing to be limiting in any manner, the cargo molecule may be a detectable agent, a therapeutic agent, a drug, a peptide, an enzyme, a protease, a carbohydrate moiety, a cytotoxic agent, one or more liposomes loaded with any of the previously recited types of cargo molecules, or one or more nanoparticle, nanowire, nanotube, or quantum dots. The cargo molecule may be linked to the antibody or fragment thereof by any suitable method known in the art. For example, and without wishing to be limiting, the cargo molecule may be linked to the peptide by a covalent bond or ionic interaction. The linkage may be achieved through a chemical cross-linking reaction, or through fusion using recombinant DNA methodology combined with any peptide expression system, such as bacteria, yeast or mammalian cell-based systems. Methods for linking an antibody or fragment thereof to a therapeutic agent or detectable agent would be well-known to a person of skill in the art.

The present invention also provides a method of detecting solid tumors, comprising administering the antibodies or fragments thereof of the present invention or the composition described above, and detecting the bound antibody or fragment thereof using a suitable detection and/or imaging technology. For example, the antibodies or fragments thereof of the present invention may be linked to a radioisotope, a paramagnetic label, a fluorophore, an affinity label (for example biotin, avidin, etc.), fused to a detectable protein-based molecule, nucleotide, quantum dot, nanoparticle, nanowire, or nanotube or any other suitable agent that may be detected by imaging methods. In a specific, non-limiting example, the antibody or fragment thereof may be linked to a fluorescent agent such as FITC or may genetically be fused to the Enhanced Green Fluorescent Protein (EGFP). The antibody or fragment thereof may be linked to the detectable agent using any method known in the art (recombinant technology, chemical conjugation, etc.).

Thus, the present invention further provides a method of detecting Her2 on solid tumors at slightly acidic pH, comprising contacting a sample (such as, but not limited to biopsy sample, or any other suitable sample) with one or more than one antibody or fragment thereof of the present invention. The antibodies or fragments thereof may be linked to a detectable agent. The Her2 antigen can then be detected using detection and/or imaging technologies known in the art, such as, but not limited to mass spectrometric or immunoassay methods. For example, and without wishing to be limiting in any manner, the antibodies or fragments thereof linked to a detectable agent may be used in immunoassays (IA) including, but not limited to enzyme IA (EIA), ELISA, "rapid antigen capture", "rapid chromatographic IA", and "rapid EIA".

The present invention also encompasses a composition comprising one or more than one antibody or fragment thereof as described herein. The composition may comprise a single antibody or fragment as described above, or may be a mixture of antibodies or fragments. The composition may also comprise a pharmaceutically acceptable diluent, excipient, or carrier. The diluent, excipient, or carrier may be any suitable diluent, excipient, or carrier known in the art, and must be compatible with other ingredients in the composition, with the method of delivery of the composition, and is not deleterious to the recipient of the composition. The composition may be in any suitable form; for example, the composition may be provided in suspension form, powder form (for example, but limited to lyophilised or encapsulated), capsule or tablet form. For example, and without wishing to be limiting, when the composition is provided in suspension form, the carrier may comprise water, saline, a suitable buffer, or additives to improve solubility and/or stability; reconstitution to produce the suspension is effected in a buffer at a suitable pH to ensure the viability of the antibody or fragment thereof. Dry powders may also include additives to improve stability and/or carriers to increase bulk/volume; for example, and without wishing to be limiting, the dry powder composition may comprise sucrose or trehalose. The composition may comprise encapsulation, time-release, or other suitable technologies for delivery of the antibody or fragment thereof. It would be within the competency of a person of skill in the art to prepare suitable compositions comprising the present compounds.

The present invention further provides a method of selectively targeting Her2-expressing cancer cells and tumor tissues, and treating solid tumors with minimal unwanted off-tumor host toxicity and a wide therapeutic window, comprising administering the antibodies or fragments thereof of the present invention or the composition described above to a subject in need thereof. Any suitable method of delivery may be used. For example, and without wishing to be limiting in any manner, the antibody or fragment thereof, or the composition, may be delivered systemically (orally, nasally, intravenously, etc.). Those of skill in the art would be familiar with such methods of delivery.

The present invention will be further illustrated in the following examples. However, it is to be understood that these examples are for illustrative purposes only and should not be used to limit the scope of the present invention in any manner.

Example 1: Computational Design of pH Dependence

The Her2-bound crystal structure of bH1-Fab was retrieved from the Protein Data Bank (entry 3BE1) [37] and structurally prepared for molecular design as described previously at physiological pH [35]. At slightly acidic pH of 5-6, visual examination was used in order to decide whether a His side chain can be protonated based on its structural environment protonation.

This led to protonation of three His residues in the antigen epitope: H497, H537 and H567, whereas the other two His residues in the antigen epitope (H490 and H542) as well as the two His residues of the Fv fragment (L-H95 and H-H35) were treated in the neutral state in the slightly acidic conditions.

Figure 9:
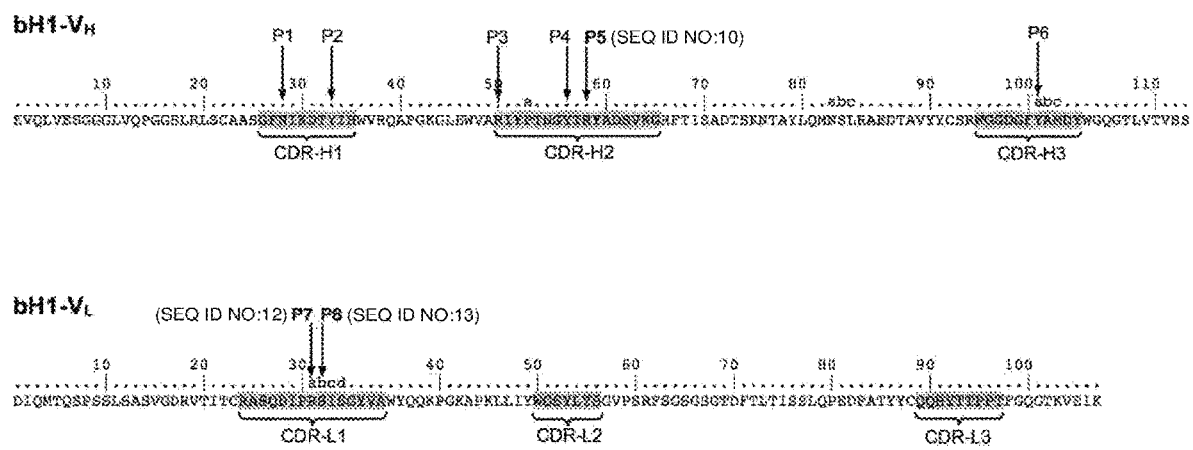
FIG. 9. Amino acid sequences of the Fv domains of the parental bH1 antibody [37]. CDR loops are shaded and labeled according to the Kabat definition, except for the CDR-H1 which is defined by the union of Kabat and Chothia definitions (the choice for the combined definition in the case of CDR-H1 was motivated by the fact that in this way a larger sequence region is subjected to histidine scanning mutagenesis so as to lead to more potentially interesting hits). Sequence numbering is according to Chothia scheme. Positions designed for single-point histidine mutagenesis are indicated by arrows and labeled according to the produced variants (see Table 1). Positions used for double-point histidine mutants are labeled in bold.

Computational His scanning was carried out with the ADAPT protocol [35] in order to generate and score single-point mutations to histidine of non-proline, non-cysteine and non-histidine residues in the CDR region covering 3 loops in the light chain: CDR-L1 (R24-A34), CDR-L2 (W50-S56), CDR-L3 (Q89-T97), and 3 loops in the heavy chain: CDR-H1 (G26-H35), CDR-H2 (R50-G65) and CDR-H3 (R94-Y104) of bH1-Fv (FIG. 9). Histidine mutations were built and evaluated energetically at these positions using the three programs, SCWRL [53-55], FoldX [56, 57] and Rosetta [58, 59] currently implemented in ADAPT [35]. From an operational perspective, since scoring functions for computational mutagenesis provide meaningful results when taken as scores relative to the parent system for which the crystal structure has been determined, the implementation of these methods in ADAPT adopts a conservative approach that limits conformational flexibility of the mutants as much as possible and especially at the level of the protein backbone atoms [58, 60].

Histidine mutations were generated at physiological pH and also in slightly acidic conditions (e.g., pH 6). For mutations at physiological pH, all programs were forced to mutate to a neutral histidine. For mutations at slightly acidic pH, each program had a different implementation of a protonated histidine. Rosetta had the simplest method in that mutations to histidine were forced to use the protonated form. In the case of FoldX, protonated histidine takes two different forms, protonated delta (called "o") and protonated epsilon (called "e"). Therefore, the mutation with the lowest FoldX stability score was retained and used for ranking. Lastly for SCWRL, the option to enable the protonated form to compete with neutral histidine tautomers was chosen. While this does not force mutation to the protonated form, if the resulting mutation is neutral it is assumed that the protonated form would be destabilizing, and vice-versa. Binding scores of the constructed His mutants relative to the parent were then calculated at each of the two pHs, $\Delta G_{Acidic}^{Mutant} - \Delta G_{Acidic}^{Parent}$ and $\Delta G_{Physiological}^{Mutant} - \Delta G_{Physiological}^{Parent}$ with the three scoring functions in ADAPT: SIE [54, 55], FoldX-FOLDEF [56] and Rosetta-Interface [58]. The double-referenced binding free energy scores, $\Delta\Delta\Delta G_{binding}$ (FIG. 1), were then derived as difference in the scores obtained in acidic conditions relative to physiological pH conditions. A consensus ranking was finally derived from these individual $\Delta\Delta\Delta G_{binding}$ scores calculated with each scoring functions. The FoldX-FOLDEF energy function [56] was also used to estimate the effect of His substitutions on the internal stability of the Fv structure at each of the two pHs. Additional technical and implementation details of ADAPT and its component methods can be found in earlier reports [35, 38, 60].

The concept of free energy optimization of a parent antibody-antigen system via mutagenesis for improved binding at acidic pH (tumor microenvironment) relative to physiological pH (normal cells) is presented schematically in FIG. 1. binding free energy gap, $\Delta\Delta\Delta G_{binding} = (\Delta G_{Acidic}^{Mutant} - \Delta G_{Physiological}^{Mutant}) - (\Delta G_{Acidic}^{Parent} - \Delta G_{Physiological}^{Parent})$, between the mutant and parent variants in the acidic relative to physiological environments. This binding free energy gap must be as negative as possible in order to enhance the selectivity for binding at acidic versus physiological pH. At the same time, the mutant must maintain a reasonable level of binding in the acidic environment relative to the parent molecule. For example, a mutant that binds 1000-fold better at acidic versus physiological pH, but has a 100 M affinity under acidic conditions, has high pH selectivity but is of limited practical use. Hence, a filter was applied to step (3) in FIG. 1 to ensure that $(\Delta G_{Acidic}^{Mutant} - \Delta G_{Acidic}^{Parent})$ is not too overly positive (e.g., not more than 2.7 kcal/mol, or 100-fold increase in $K_D$). Moreover, since the designed mutants must be stable in the intended acidic environment, another filter was applied to the folding free energy associated with step (3). This ensures that the stability of the mutant is comparable with that of the parent, and hence the predicted $\Delta\Delta G_{folding} = \Delta G_{folding}^{Mutant} - \Delta G_{folding}^{Parent}$ should typically be less than 2.7 kcal/mol [35]. For manufacturing and in vivo delivery reasons, stability at physiological pH should also be maintained, and so $\Delta\Delta G_{folding}$ at that pH associated with step (4) in FIG. 1 should not be overly positive either.

We have implemented this version of ADAPT [35, 38] capable of handling dual-pH His-scanning mutagenesis, and applied it to the bH1 Fab in complex with Her2 ectodomain [37](WO2008027236; WO2010027981; WO2010108127; WO2015095539). A total of 68 positions (non-His, non-Pro, non-Cys) forming the CDR loops of bH1 (FIG. 9) were screened for single mutations to His with 3 protocols for mutant generation and relative binding affinity scoring, and with one protocol for relative stability scoring (Table 1). 21 mutants were excluded based on stability criteria on acidic conditions (>2.72 kcal/mol from parent). From the remaining 47 mutations, the top 10 in average ranks in terms of $\Delta\Delta\Delta G_{binding}$ binding affinity gap were retained. Ranks 1 (L-R30a), 2 (H-R58), 6 (H-N28), 8 (H-Y100a) and 10 (H-Y56) were pursued further. The other 5 mutations were excluded after visual examination of the modeled 3D structures, namely rank 3 (H-G97) due to steric clashes, rank 4 (L-Y92) due to packing of protonated His in a hydrophobic environment, and ranks 5 (H-N54), 7 (L-S30d) and 9 (H-K64) for which the introduced His residues made no direct contacts with the antigen. Rank 26 (L-S30b) was included based on its second-best stability in acidic conditions. Rank 30 (H-Y33) was also included as another test of a non-highly-ranked mutant. These two mutants from the bottom half of the ranked list passed visual inspection in terms of good steric and electrostatic interactions in the complex. Lastly, H-R50 was included as another control, having the best average rank for binding affinity change if the stability filter under acidic conditions would not be applied.

Figure 2:
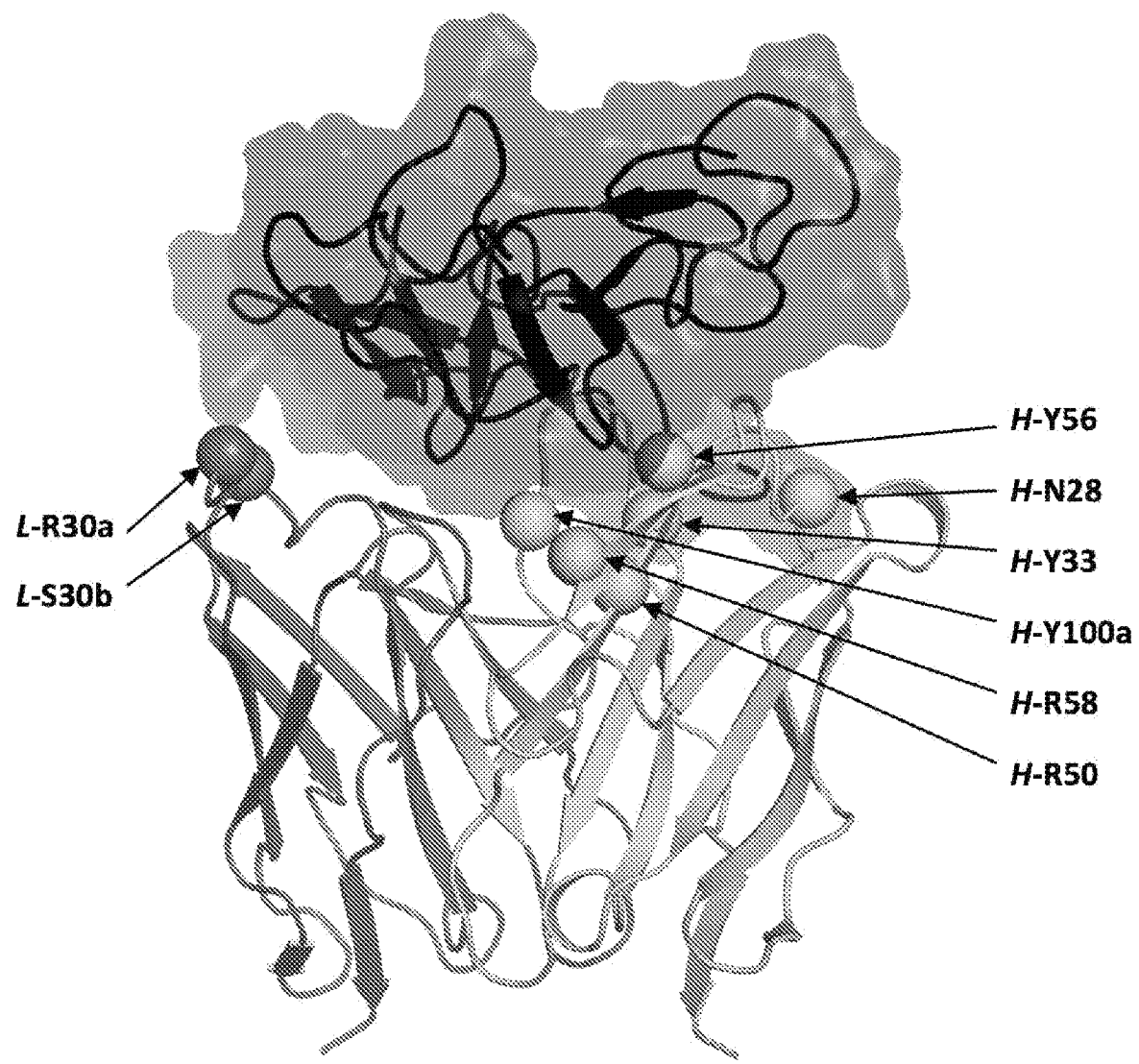
FIG. 2. Structural location of selected histidine mutations. Shown is the crystal structure of the parental bH1-Her2 complex (PDB code 3BE1) [37] as prepared for molecular simulations. Only the antigen-binding Fv domains of the antibody are shown. Selected positions for mutation to histidine are shown as Cα-sphere models and are labeled. Domain IV (residues C489-N607) of the Her2 antigen including the epitope is rendered as a black ribbon inside a translucent gray molecular surface.

These selected residues for single-point mutations to histidine are spread out over four of the six CDR loops (FIG. 9). Having widely separated mutations at the antibody-antigen interface (FIG. 2) can be beneficial for combining them into higher-order mutants using the ADAPT protocol. This is based on reasonable additivity of contributions from spatially separated mutations to binding affinity [35, 38].

Example 2: Protein Expression and Purification cDNA for the heavy and light chains of Fab and full-size human IgG1/k antibody variants were ordered from commercial vendors (ThermoFisher Scientific/Life Technologies Inc., Burlington, ON; GENEART, Regensburg, Germany). These contained signal peptide sequences, but no His-tags. Productions were carried out by co-transfection of CHO-3E7 cells as described previously [35] at 200-mL scale. Transfections were performed at a cell density between $1.8 \times 10^6$ to $2.0 \times 10^6$ cells/mL with viability greater than 98%. Cells were distributed in 1.0 L to 2.8 L-shaker flasks and transfected with 1 µg of total DNA per 1 mL of production (50% of total DNA contained heavy chain and light chain constructs at ratios of 1:1 (w/w)) using PEI MAX™ (Polysciences, Inc., Warrington, PA). The final DNA:PEI MAX™ ratio was 1:4 (w/w). Cell cultures were incubated for 24 h on an orbital shaking platform at an agitation rate of 110 rpm at 37° C. in a humidified 5% $CO_2$ atmosphere. Twenty-four hours later, the cultures were fed with Tryptone N1 at 1% w/v final and Valproic acid sodium salt at 0.5 mM final concentration and transferred to 32° C. for 6 days. Cell density and cell viability were determined by direct counting of cell samples with a Vi-CELL automated cell counting system (Beckman Coulter Life Sciences, Indianapolis, IN) using the trypan blue dye exclusion method.

Purifications from cell-culture supernatants were performed by protein-A affinity chromatography for Fab fragments and the IgG1/k full-size antibodies (FSAs). Purifications of cell-culture supernatants were performed by loading the Fabs onto 5-mL MabSelect or 1-mL HiTrap MabSelect columns (GE Healthcare Life Sciences, Mississauga, ON) and FSAs onto MabSelect SuRe columns (GE Healthcare) equilibrated in HyClone™ Dulbecco's phosphate-buffered saline (DPBS; GE Healthcare Life Sciences). Columns were washed with PBS and Fabs or FSAs were eluted with 100 mM citrate buffer pH 3.0, respectively. Fractions containing Fabs or FSAs were pooled and the citrate buffer was exchanged against DPBS on CentriPure P100 columns (EMP Biotech, Howell, NJ) or ZebaSpin TK MWCO columns (ThermoFisher Scientific, Waltham, MA).

Purified Fabs and FSAs were sterilized by filtration through 0.2 µm filters. UPLC-SEC was used to assess the purity of all eluates. Variants with less than 95% purity (Fab fragments bH1-P4, bH1-P6, bH1-P5P7 and bH1-P5P8) were further purified by preparative size exclusion chromatography (SEC) on Superdex-200 increase columns (GE Healthcare Life Sciences). Selected peak fractions were concentrated by ultrafiltration using Vivaspin® Turbo 4 or 15 (depending on the volume to concentrate) centrifugal concentrator with a membrane molecular weight cut off of 10 kDa (GE Healthcare Life Sciences) at room temperature following the manufacturer's instructions. During the process, the protein concentration was monitored on a Nano-Drop™ 2000 spectrophotometer (ThermoFisher Scientific) using absorbance at 280 nm and the calculated specific extinction coefficient of each variant.

Example 3: Surface Plasmon Resonance (SPR) Binding Affinity Measurements of pH-Dependent Binding to Recombinant Her2 Ectodomain Fab-Her2 interactions were analyzed using a Biacore™ T200 (GE Healthcare, Missisauga, ON) surface plasmon resonance instrument. Samples were assayed at 25° C. or 37° C. using PBS containing 0.05% Tween 20 (Teknova, Hollister, CA) with added 3.4 mM EDTA as running buffer or 150 mM citrate-phosphate buffer pH 5 with added 3.4 mM EDTA, 135 mM NaCl and 0.05% Tween 20. Recombinant human Her2 extracellular domain (ThermoFisher Scientific, Burlington, ON) was immobilized onto a CM-5 sensorchip along with a mock-activated blank control surface for referencing. Her2 was diluted to 10 µg/mL in 10 mM NaOAc immobilization buffer pH 4.5 (Biacore) and immobilized to approximately 200 RUs using the Biacore control software Immobilization Wizard with standard NHS/EDC amine coupling. The Her2 interaction was determined using single cycle kinetics analysis for each variant with five concentrations using 3-fold dilutions from the top concentration between 100 to 900 nM depending on the affinity of the variant. Fab samples were injected at 100 L/min with a contact time of 90 s and a 1200-s dissociation using either pH 5.0 or 7.4 running buffer. Sensorgrams were double referenced to the mock-activated blank sensor surface and analyzed for kinetic determination using a 1:1 binding model in BiaEvaluation software v3.1 (GE Healthcare).

The parental and selected bH1-Fab variants were first tested for binding to recombinant Her2 ectodomain by SPR at the physiological pH of 7.4 as well as at pH 5.0, whereby the Fab samples were flowed over the antigen ectodomain immobilized at a sensor-chip surface. Interestingly, parental bH1-Fab bound to the Her2 ectodomain about 4 times weaker at acidic pH ($K_D$=13±4 nM) versus physiological pH ($K_D$=3±1 nM) due to a combination of a slower on-rate and a faster off-rate (Table 2). In contrast, our rank-2 computational structure-based designed variant bH1-P5 (SEQ ID NOS:14,15) having the H-R58 amino-acid residue mutated to histidine showed improved antigen binding at acidic pH ($K_D$=98±30 nM) versus physiological pH ($K_D$=310±8 nM). In free energy terms, reversal by the new mutant of the undesired binding phenotype of the parental Fab to the desired pH dependence resulted from a negative value for $\Delta\Delta\Delta G_{binding}$ of −1.54 kcal/mol. This indicates a successful design in the desired direction for pH dependence, and is clearly apparent in the iso-affinity plot in FIG. 3. Here, we see the opposite directions of binding free energy change by shifting the pH from physiological to acidic, and comparing the parental bH1-Fab to the bH1-P5 and other variants.

Figure 3:
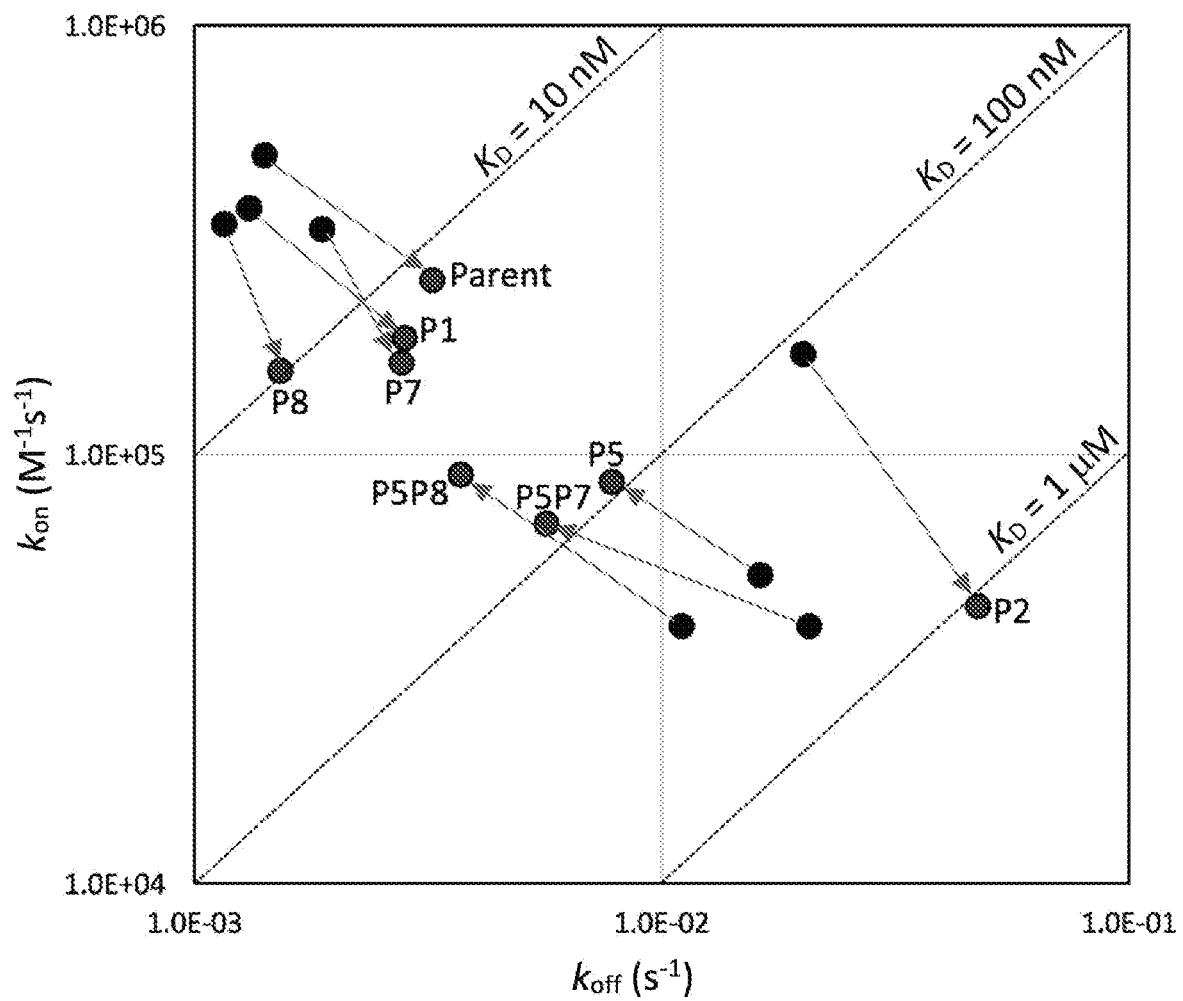
FIG. 3. Iso-affinity plots from SPR data. Arrows indicate moving the data point on the iso-affinity plot from physiological to acidic environments for various variants (labeled, mean data from Table 2).

By the $\Delta\Delta\Delta G_{binding}$ objective metric, other successful designs were bH1-P7 (L-R30aH) and bH1-P8 (L-S30bH), although in these cases the undesired binding phenotype of the parent was not reversed but merely weakened. These are also apparent in the iso-affinity plot (FIG. 3). Variant bH1-P1 (H-N28H), ranked 6 computationally, was similar to the parent, whereas for bH1-P6 (H-Y100aH, ranked 8) had complex binding and poor fit at acidic pH. For variant bH1-P2 (H-Y33H, ranked 30) the parental phenotype was actually accentuated and hence this variant had a positive value for $\Delta\Delta\Delta G_{binding}$ (Table 2). Finally, binding was so weak that it could not be detected at one or both pHs for variants bH1-P4 (H-Y56H, ranked 10) and bH1-P3 (H-R50H, control for testing a case with high destabilization predicted at acidic pH). As this SPR binding analysis was carried out at 25° C., we repeated experiments at 37° C. and obtained similar trends, with almost identical equilibrium constants and slightly higher rate constants as expected from Arrhenius equation.

Figure 4:
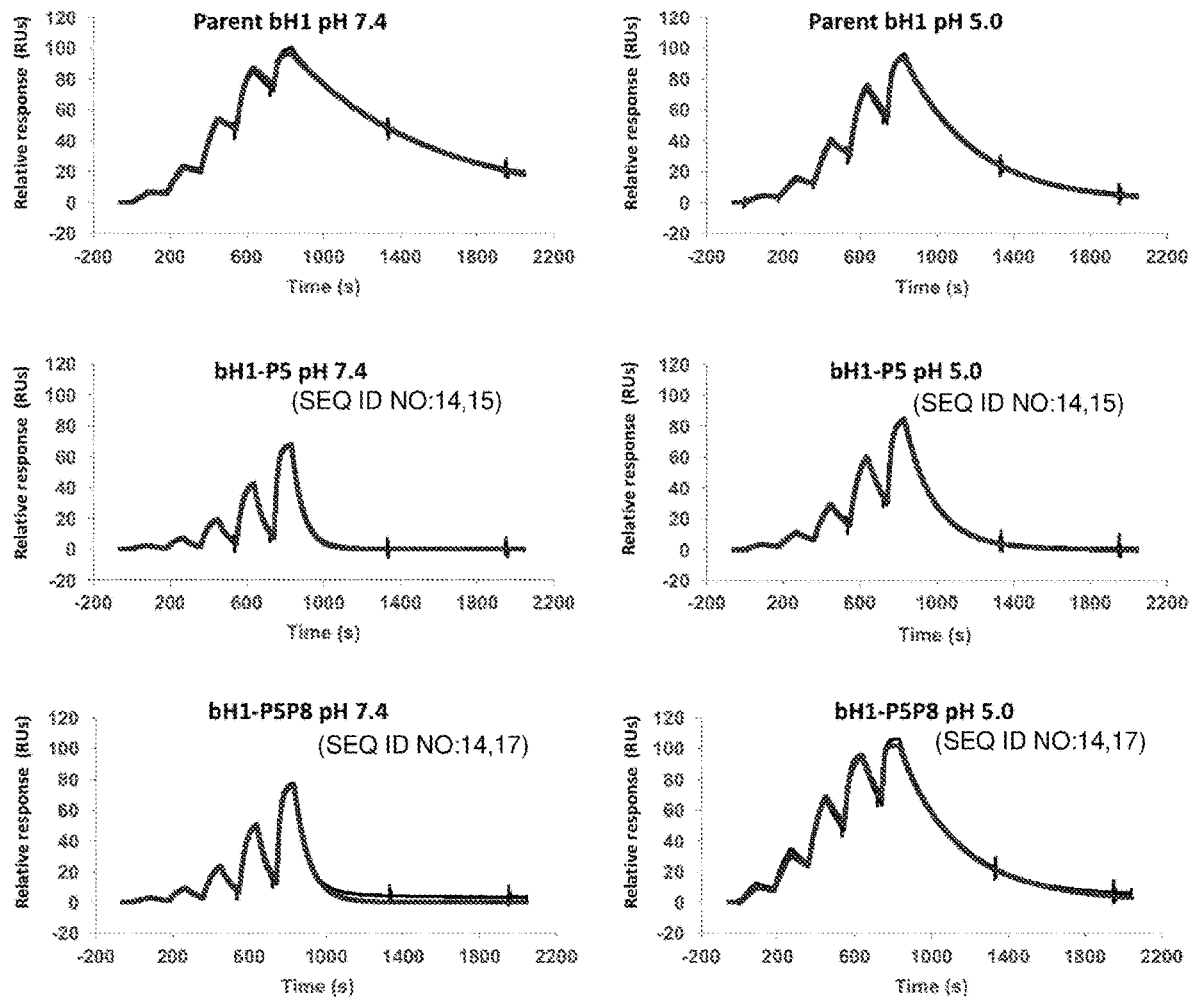
FIG. 4. Representative SPR sensorgrams for select Fab variants. Interaction of the parent bH1-Fab, the lead single mutant bH1-P5 (H-R58H) (SEQ ID NOS:14, 15) and the double mutant bH1-P5P8 (H-R58H,L-S30bH) (SEQ ID NOS:14,17) with immobilized Her2 ectodomain.

Based on the SPR data for single mutants, three designed bH1 variants, bH1-P5, bH1-P7 and bH1-P8, were selected for generation of double mutants bH1-P5P7 (H-R58H,L-R30aH) (SEQ ID NOS:14,16) and bH1-P5P8 (H-R58H,L-S30bH) (SEQ ID NOS:14,17). These double mutants combine well-spaced mutations present on distinct chains, aiming at introducing additivity of mutation effects. The SPR-based $\Delta\Delta\Delta G_{binding}$ values listed in Table 2 confirm that additivity has been achieved. Both double mutants had approximately 6-fold stronger antigen binding at acidic pH than at physiological pH. This behavior was significantly driven by faster dissociations (larger $k_{off}$) at physiological pH than at acidic pH, in sharp contrast to the parent, as also apparent in the iso-affinity plot (FIG. 3). By comparing the variant bH1-P5P8 (SEQ ID NOS:14, 17) with the parental bH1-Fab, we see that antigen binding in the acidic environment has only marginally weakened ($K_D$ of 50±20 nM versus 13±4 nM, respectively) whereas binding affinity in the physiological pH environment has been weakened by 2 orders of magnitude ($K_D$ of 290±50 nM versus 3±1 nM, respectively). This is also readily seen by visual inspection of the corresponding SPR sensorgrams shown in FIG. 4.

Example 4: Flow Cytometry Measurements for pH-Dependent Binding to Cells Expressing Intact Her2

SKOV3 and JIMT-1 cells (ATCC) were cultured in McCoy's 5A and DMEM media, respectively, supplemented with 10% fetal bovine serum (FBS).

Cells in T-75 flasks were washed twice with D-PBS and then dissociated using Cell Dissociation buffer (Sigma, C5914) at 37° C. The cells were centrifuged and resuspended in the appropriate pH binding buffer; RPMI-1640 media, 2% FBS, 50 mM BES (Sigma), at the indicated pH ranging from pH 5.2 to 7.3, and then dispensed at 1×10⁵ cells/well in a 96-well polypropylene (PP) v-bottom plate (Costar) at 4° C. Pre-diluted Fab or full size antibody samples were then added to cells to give concentrations ranging from 0.02 to 300 nM (8-point dilution series) in a final volume of 100 L/well, followed by incubation at 4° C., 2 h. The cells were then washed twice by centrifugation at 233×g, removal of supernatant by aspiration and resuspending the cells in 200 L binding buffer at 4° C. Detection reagent, either anti-human Fab or Fc AlexaFluor488-(Fab')$^2$ (Jackson Immunochemicals, West Groove, PA), was then added at a final concentration of 10 g/mL and samples were incubated at 4° C., 1 h. The cells were washed twice in 200 µL binding buffer, followed by addition of 120 µL 1.0% propidium iodide and samples were then transferred to Multiscreen 96-well plates (60 m Nylon Mesh, Millipore, Etobicoke, ON) and filtered by centrifugation. The filtrate samples were collected from the Multiscreen receiver plate and transferred to a new V-bottom polypropylene plate at 4° C. Flow cytometric analysis was performed on a BD LSR-Fortessa instrument (BD Biosciences, San Jose, CA). The AlexaFluor488 fluorescence was measured using a 488 nm laser as excitation source and a 530/30 nm band pass filter. Median fluorescence intensity (MFI) was reported by analyzing 3000 alive cells per sample with the gating strategy: all cells/singlets/alive cells (PI negative) using BD FACS-Diva software (BD Biosciences).

Figure 5:
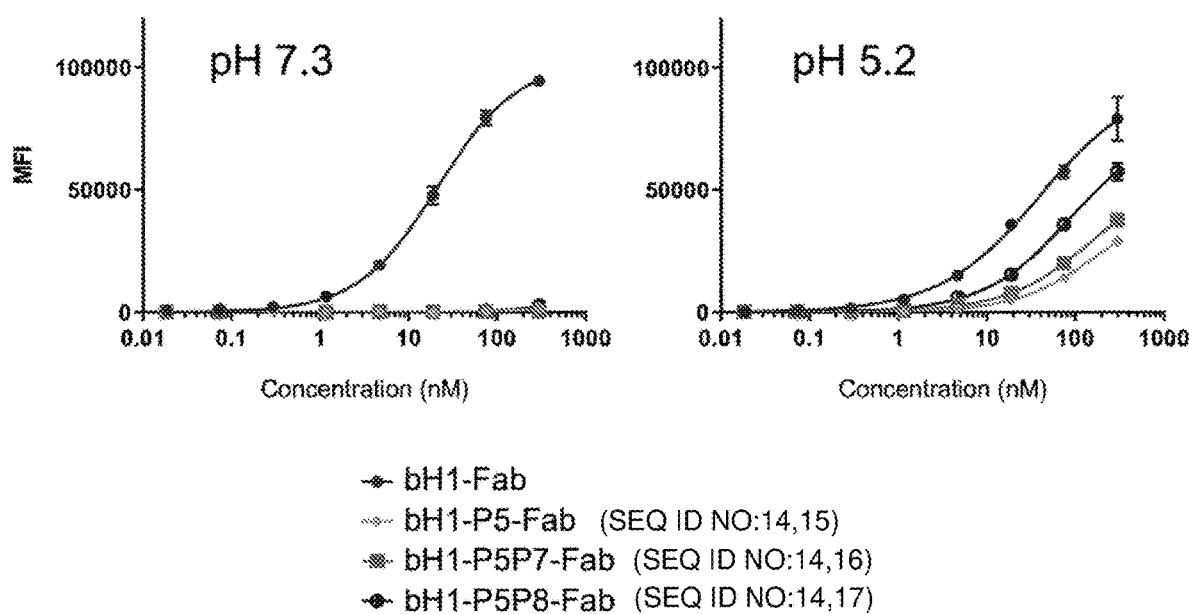
FIG. 5. pH dependence of Fab variants binding to Her2-expressing SKOV3 cells. Selected anti-Her2 Fab variants at varying concentrations were analyzed for cell-based binding by flow cytometry under acidic and physiological pH conditions.
Figure 10:
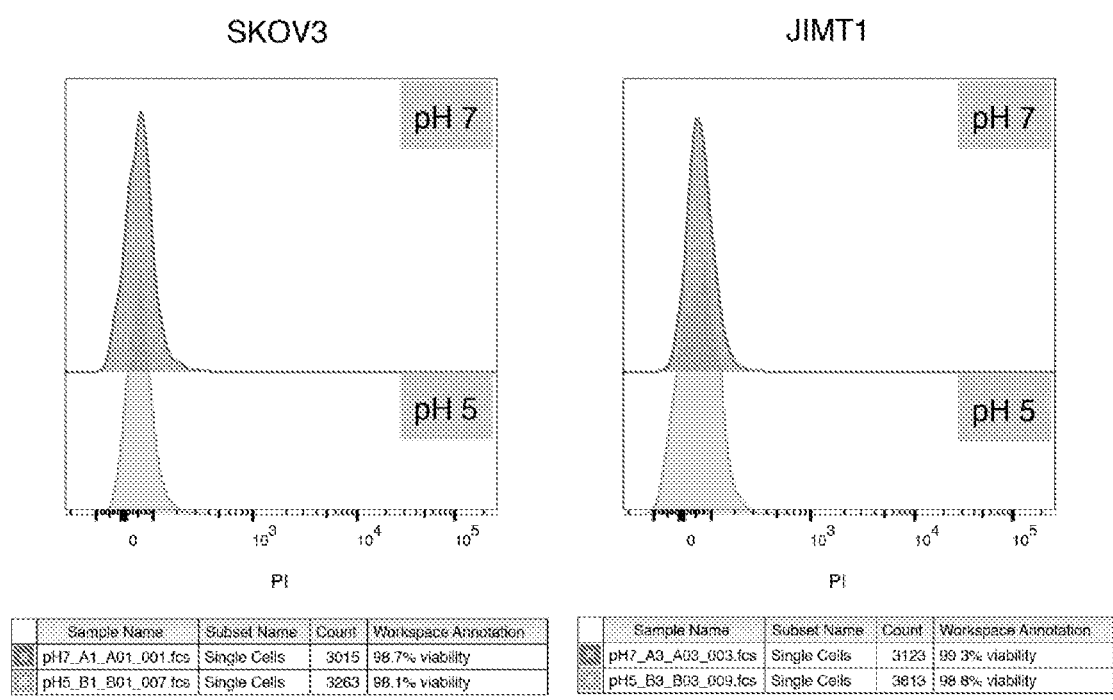
FIG. 10. Viability test of SKOV3 and JIMT1 cells at pH 5 and pH 7. Cells were incubated during 3 h at 4° C. in RPMI-1640 2% FBS 50 mM BES buffer adjusted to pH 7 or pH 5 (similar conditions to the complete binding assay). Cells viability was evaluated by flow cytometry using PI 1% staining.

Encouraged by the SPR binding data on the recombinant Her2 ectodomain, we examined the most promising designed bH1-Fab variants bH1-P5 (SEQ ID NOS:14, 15), bH1-P5P7 (SEQ ID NOS:14,16) and bH1-P5P8 (SEQ ID NOS:14,17) for pH dependence of binding to cells expressing intact Her2. At the high Her2 cell surface density of the SKOV3 cells, the parent bH1-Fab binding was approximately 2-fold weaker at acidic pH ($K_D$ of ~41 nM) than at physiological pH ($K_D$ of 21 nM) (Table 3). In contrast, while weak binding of the designed Fab mutants to SKOV3 cells could be detected at pH 5.2 ($K_D$ range ~100-200 nM), their binding, if any, was weaker than the sensitivity of our detection method at pH 7.3 (FIG. 5). The double mutant bH1-P5P8 Fab (SEQ ID NOS:14, 17) was found to have ~2-fold stronger affinity than bH1-P5 (SEQ ID NOS:14,15) and bH1-P5P7 (SEQ ID NOS:14,16) at acidic pH. Similar results were obtained on the JIMT-1 cell line expressing Her at lower density than SKOV3 cells (data not shown). The viability of various cell lines under acidic (pH 5.2) and physiological (pH 7.3) conditions was tested and shown to be not affected by the conditions used in the binding assay (FIG. 10).

Figure 6A:
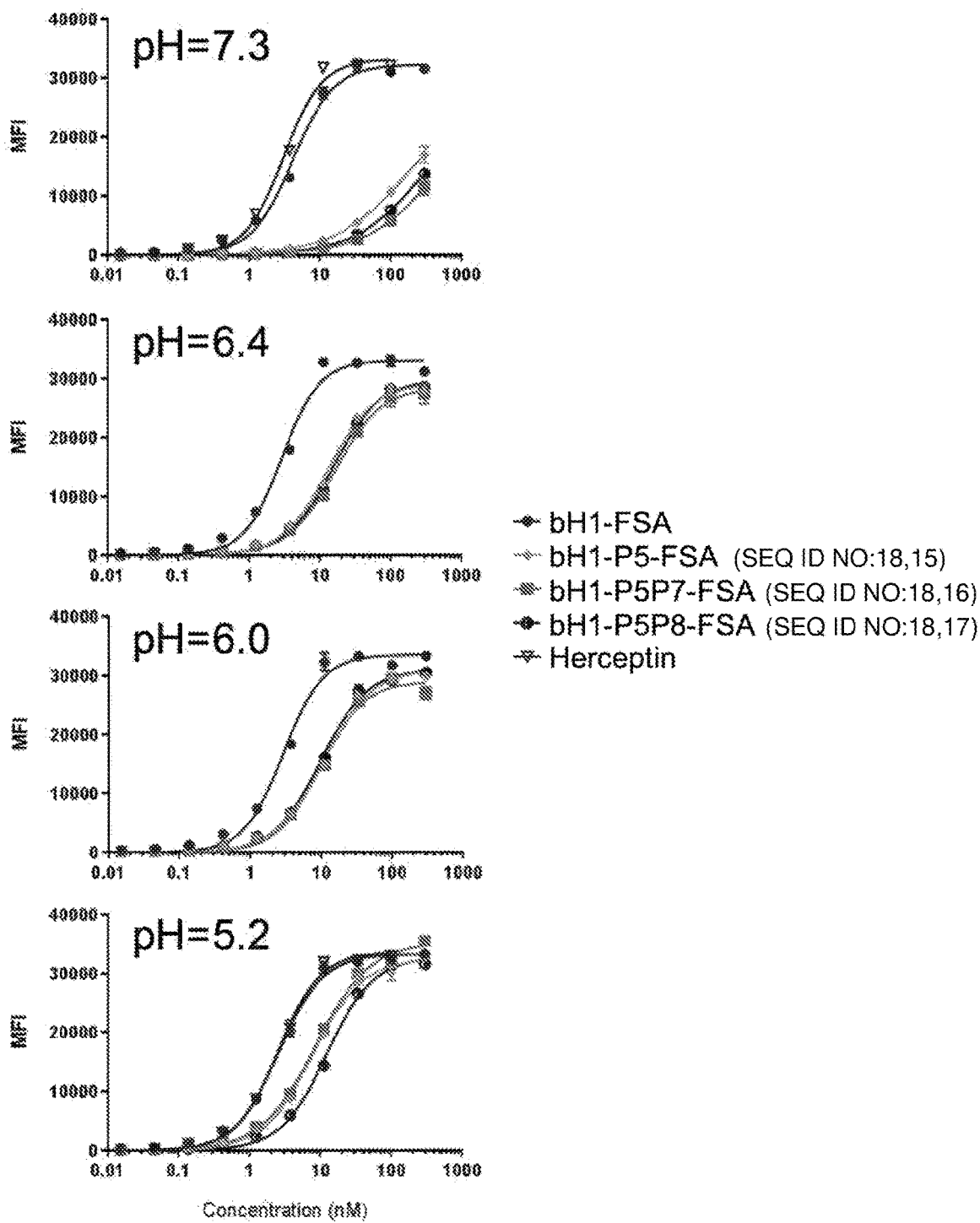
FIGS. 6A and 6B. pH dependence of FSA variants binding to cells expressing Her2.
Figure 6B:
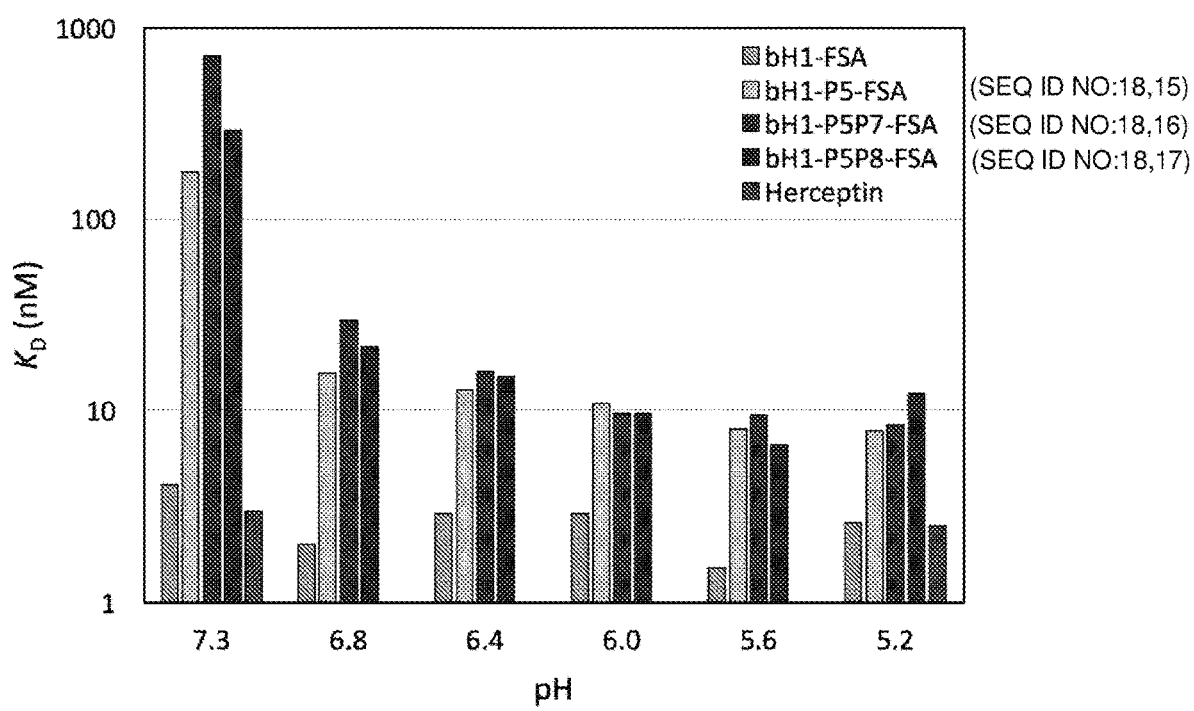

The designed variants were then reformatted into human IgG1/k FSAs and re-tested on the high-density Her2 cells. A pH scan of SKOV3 cell binding within the 5.2-7.3 range is shown in FIG. 6A for designed FSA variants and control antibodies. The parental bH1-FSA displayed low-nM apparent affinity similar to the related antibody Herceptin at physiological pH (apparent $K_D$ of 4 nM and 3 nM, respectively, Table 4), suggesting that the weaker cell-based binding previously seen with the bH1-Fab ($K_D$~20 nM, Table 3, FIG. 5) could be improved by avidity binding. Both parental bH1-FSA and Herceptin displayed practically no pH-dependent cell binding, with apparent $K_D$ values relatively stable within the 2-4 nM range between pH 5.2 and pH 7.3. The designed FSA mutants also maintained significant cell-surface Her2 binding in the acidic range of pHs, from pH 5.2 up to pH 6.0 ($K_D$ range 8-12 nM), with some weakening of affinity in the pH 6.4-6.8 range to 13-30 nM. Importantly, further increasing the pH to 7.3 led to a marked drop of binding capacity of the designed variants well above an apparent $K_D$ of 100 nM (Table 4), which is in sharp contrast to the pH-independent binding observed with the parental bH1-FSA and Herceptin. Hence, we were successful in designing a Her2 directed antibodies that showed more than 10-fold pH-selectivity for SKOV3 cell binding at pH 6.0 over pH 7.3 conditions, and ~25-fold selectivity at pH 6.8 over pH 7.3. The observed cell binding dependence on pH for the designed mutants (FIG. 6B) is consistent with the histidine pKa value of ~6.4 [15].

Figure 8:
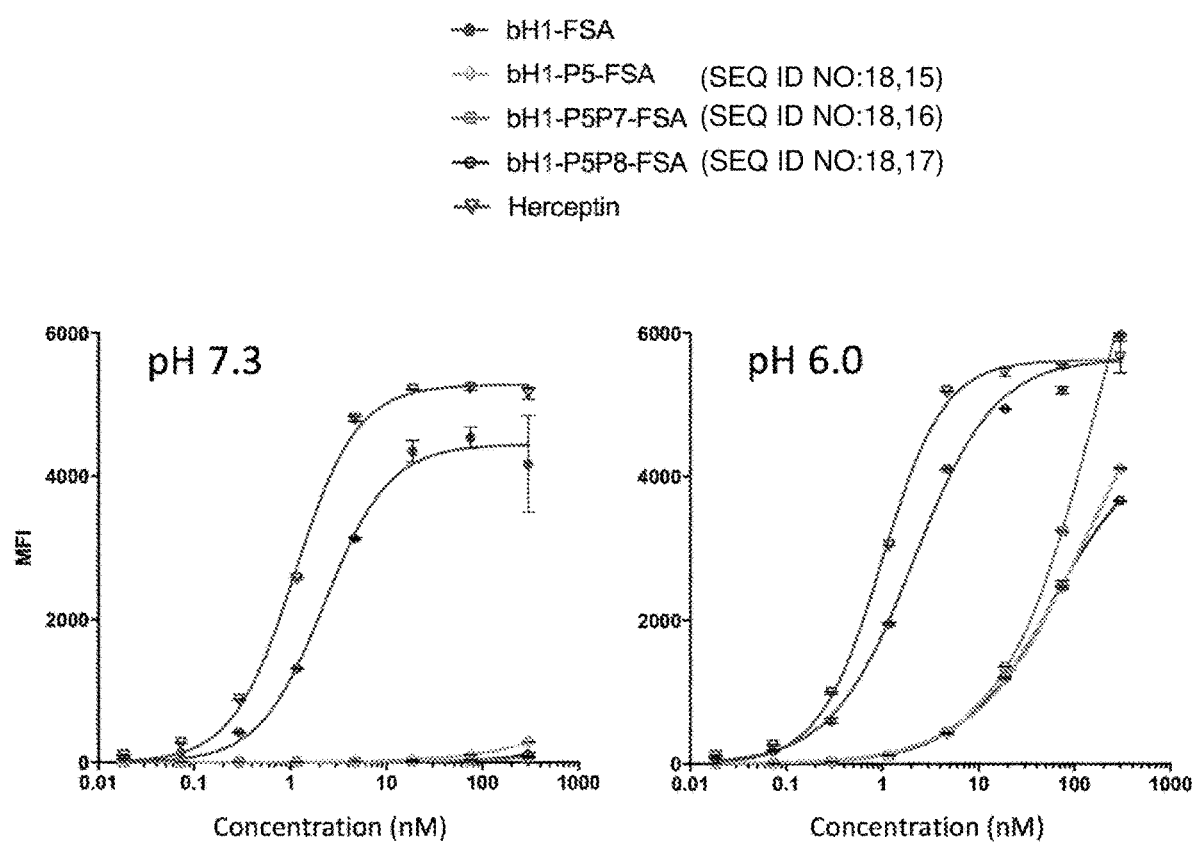
FIG. 8. pH dependence of designed FSA variants binding to cells expressing Her2 at low density. Low-density Her2 expressing JIMT-1 cells were tested under acidic and physiological pH conditions and cell binding was analyzed by flow cytometry. The left panel representing binding to the normal cell model (low-density Her2 and physiological pH) is to be compared with binding of the same variants to the tumor cell model consisting of high-density Her2 (SKOV3 cells) within a pH range of 6.0-6.8, as presented in FIG. 6A.

The ability of Herceptin and the related bH1-FSA to equally engage Her2-expressing cells at slightly acidic pH typical of solid tumors as well as at physiological pH typical of normal tissues (FIG. 6) may result in unwanted systemic toxicity to the host. Histidine mutants derived from the bH1-FSA designed in this invention have more than 10-fold weaker binding at pH 7.3 than at pH 6.0 while still possessing fairly strong binding within the pH 6.0-6.8 range ($K_D$ below 30 nM) to high Her2-density tumor cells. To further determine the tumor selectivity of these antibodies, we evaluated their binding on Her2-expressing JIMT-1 cells (i.e., ~$10^4$ Her2 receptors per cell, representing a lower Her2 density similar to Her2-expressing cardiac cells 30 [61]) at physiological pH. As it can be seen in the left panel of FIG. 8, Herceptin and bH1-FSA bind very well to the surface of these cells at pH 7.3. In sharp contrast, the designed antibodies, and especially the double-point His mutants, advantageously completely lost their binding in these normal cell conditions even at the highest tested concentration of 300 nM (~45 µg/mL). Here, the pH-dependent binding mechanism works in concert with weakened avidity effects in order to completely eliminate off-tumor targeting and widen the selectivity for tumor versus normal tissue. pH-dependent binding of the His-mutant bH1-FSAs was also present on the low-Her2 JIMT-1 cells, with estimated KDs greater than 50 nM at pH 6.0 (FIG. 8, right panel), albeit it more closely mirrored the pH-dependent binding of Fabs on high-Her2 cells due to lack of avidity effects. This data also suggests reduced off-tumor targeting of normal tissues living under acidic pH (e.g., Her2 expressed on normal gastric epithelia) relative to Herceptin and parental bH1-FSA.

Anti-Her2 antibodies with pH-dependent binding selectivity towards slightly acidic pH such as those disclosed here can be adapted to other formats suitable for various therapeutic modalities. One of the most urgently needed is as antibody-drug conjugates (ADCs) since those carry toxic payloads with potential for widespread cytotoxicity [62, 63]. Another format that would benefit from pH-selective antibodies is that used in the radioimmunotherapy (RIT) of solid tumors, especially when a compartmental route of administration is not feasible and systemic application leads to radiation exposure to non-target organs. The fact that the Fab fragments of the designed variants possess monovalent binding in the Fab format at acidic pH with no binding at all at physiological pH (FIG. 5) indicates that they may also be used as targeting moieties in bispecific antibodies. Furthermore, a heterodimeric IgG framework can be augmented by multivalent presentation of the pH-sensitive Fab arm for increased potency through avidity (e.g., 1Fab-IgG) [2, 42]. The Fab and FSA can be reformatted into other antibody formats, for example, but not limited to single-chain variable domains (scFv) [64], and scFv's for generation of chimeric antigen receptors (CARs) [48]. The 2D-tethering of CARs on the T-cell membrane may also complement their pH-dependent binding with avidity-driven selectivity towards tumor cells. The advantages provided by these novel anti-Her2 pH dependent variant antibodies confirm that well established antibodies that target cancer cells can be improved, and the improvements, as now provided, can help to better target tumour cells and to reduce toxicity associated with such treatments. The promising results now provided confirm that a computational structure-based engineering of pH-selectivity can be successfully employed to other high-profile cancer targets with the aim of delivering safer immunotherapies in oncology.

Example 5: Structural Interpretation of pH-Dependent Binding

Figure 7:
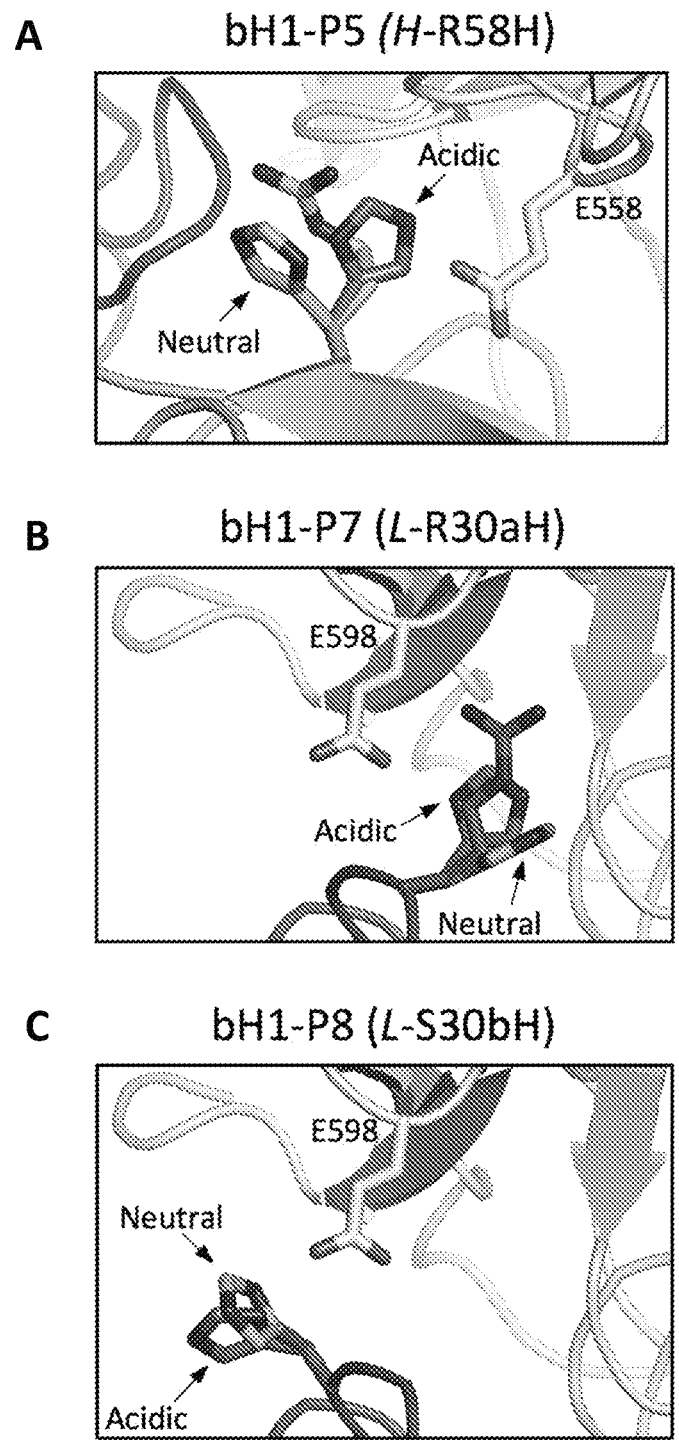
FIG. 7. Structural details of best single-point histidine mutants are provided in panels (A), (B) and (C) for mutants P5, P7 and P8 respectively. Antibody chains of the parental bH1 antibody are colored in dark gray, and the antigen is rendered in light gray. At each mutated position, the parental side chain and its histidine side chain substitutions in the acidic and physiological pH conditions are overlaid and rendered as dark-gray sticks model. Arrows indicate histidine mutation in the acidic and neutral states. The main interacting side chains of the antigen are also shown in dark-gray sticks models and labeled by residues numbers.

One of the advantages of rational structure-guided affinity maturation is that it helps to understand the structural basis for improvement of binding affinity. For designing the type of pH-dependent binding pursued in this study, the ideal scenario is to weaken binding in the physiological pH environment (negative design) and strengthen binding in the acidic environment (positive design) relative to the parent, as exemplified in FIG. 1. Scenarios based only on positive designs or only on negative designs in both environments are also viable. It is likely that available optimization routes will be system dependent. In the bH1-Her2 system investigated here, the pH selectivity of the bH1-P5 mutant H-R58H arises from negative designs at both pHs, with the impact being marginal at acidic pH and large at physiological pH (see FIG. 3, Tables 2-4). Molecular modeling suggests that replacing arginine for histidine at position H-58 may incur some modest cost in non-polar packing in both environments due to a relatively crowded location at the antibody-antigen interface. From an electrostatic viewpoint, this mutation may have minimal impact in the acidic environment where the positive charge is maintained and favorable interaction with the negatively charged E558 could be established, but it may incur a larger cost in the physiological environment that eliminates that positive charge (FIG. 7A). A similar mechanism underlies the bH1-P7 mutant L-R30aH, but the negative design is attenuated relative to P5 due to its more exposed location. Hence, for bH1-P7, the small effect (see FIG. 3) of negative design at physiological pH is predicted to arise from removal of positive charge and loss of electrostatic interactions with the negatively charged E598 (FIG. 7B). The case of bH1-P8 mutation L-S30bH seems to be different, as the SPR and cell-binding data for the bH1-P8 mutant versus parent, as well as between the bH1-P5P8 and bH1-P5 mutants (see FIGS. 3 and 5) appear to signal a small degree of positive design under acidic conditions. A charged His residue at this position can interact more favorably with E598 than the parental neutral residue Ser (FIG. 7C).

Example 6: Biophysical Characterization of pH Sensitive Antibody Variants

In order to verify that the designed His mutations do not introduce protein folding instability or aggregation relative to the parental bH1 antibody, differential scanning calorimetry (DSC) and sedimentation velocity (SV) analytical ultracentrifugation analyses were carried out.

DSC was used to determine the thermal transition midpoints ($T_m$) of bH1-FSA variants using a VP-Capillary DSC system (Malvern Instruments Ltd, Malvern, UK). Samples in DPBS buffer were diluted in the DPBS buffer to a final concentration of 0.4 mg/mL. Aliquots of each variant were buffer exchanged to 20 mM sodium acetate, 150 mM NaCl, pH 5.1 using 0.5 mL, 7 kDa MWCO ZebaSpin columns (ThermoFisher Scientific) according to the manufacturer's instructions. Samples in acetate buffer were diluted in the acetate buffer to concentrations of 0.15-0.25 mg/mL to accommodate sample availability. Thermal denaturation was carried out by increasing the temperature from 20° C. to 100° C. at a rate of 60° C./h, with feedback mode/gain set at "low", filtering period of 8 s, pre-scan time of 3 min, and under 70 psi of nitrogen pressure. All data were analyzed with Origin 7.0 software (OriginLab Corporation, Northampton, MA). Thermograms were corrected by subtraction of corresponding buffer blank scans and normalized to the protein molar concentration. The $T_m$ were determined using a manual fit to three transitions.

SV analytical ultracentrifugation experiments were performed on a Beckman XL-I analytical ultracentrifuge monitoring absorbance at 280 nm. Full-size antibodies, with the exception of bH1-FSA, were diluted to an $A_{230}$ of 0.5 with a pathlength of 0.3 cm. Material availability required that bH1-FSA be diluted to an $A_{230}$ of 0.3. Two sector charcoal-filled epon centerpieces were used with the appropriate buffer loaded into the reference sector. Samples were sedimented at 40,000 rpm using an 8-hole rotor at 20° C. with absorbance scans collected every four minutes. The c(s) distributions were obtained from scans 1-63 using SEDFIT software and were integrated using GUSSI software.

Data listed in Table 5 shows similar biophysical properties for all bH1-FSA variants at both pH 5.1 and pH 7.2. All variants behave similarly in each buffer. The DSC data shows that for each variant $T_m1$ (CH2-domain melting) occurs at ~65° C. in acetate buffer and at ~70° C. in DPBS. Comparing results in acetate buffer and DPBS, $T_m2$ (Fab melting) and $T_m3$ (CH3-domain melting) differ by ~2 degrees and 1 degree, respectively, for each variant. Since binding of engineered variants is decreased at physiological pH relative to acidic pH despite slight thermal stabilization of these variants at pH 7.2 compared to low pH, the binding differences cannot be due to molecular stability differences resulting from the engineered mutations. The SV data shows that for each variant in each buffer, the major peak accounting for 84-90% of the total peak area is at 6.4-6.5S, consistent with monomeric antibody. Each variant has a minor peak at 8-10S, consistent with dimeric antibody, accounting for 3-6% of the total peak area. Given the similar size distributions at pH 5.1 and at pH 7.2, the binding differences observed for the engineered variants between physiological and acidic pHs cannot be attributed to differences in aggregation.

Example 7: Spheroid Growth Inhibition Functional Testing

Human breast invasive ductal primary carcinoma BT474 cells purchased from (ATCC) were grown in McCoy's 5A medium supplemented with 10% FBS. Acidosis adapted cells (BT474-AA) were cultured and maintained in pH adjusted medium at pH 6.4 for 3 months. The pH of the medium was altered by adjusting the sodium bicarbonate concentration in the base medium to achieve the desired pH. Culture media were equilibrated at 37° C. and 5% CO2 for at least 12 h prior to use. Spheroid growth inhibition in response to the Herceptin pH selective and none selective variants were then tested for cells grown in normal pH, cells grown in normal pH but exposed acutely to pH 6.4 conditions for the duration of the experiment and low pH adapted cell lines. The cells were seeded in 96-well PrimeSurface 3D Culture Spheroid plates (S-BIO, Hudson, NH) at 1000 cells per well for 72 h prior to the addition of antibodies. Spheroids were then supplemented with adjusted concentrations of antibodies diluted in the culture media at pH 7.4 or pH 6.4. Spheroid growth was monitored over 8 days and images were captured every 6 h using IncuCyte S3 (Essen BioScience, Ann Arbor, MI). Spheroid segmentation and size measurements were conducted using the IncuCyte software, following instrument guidelines. Spheroid sizes were then normalized to time zero and to the human IgG1 isotype control antibody (BioXCell, West Lebanon, NH, Cat #BE0297) treated spheroids.

Figure 11:
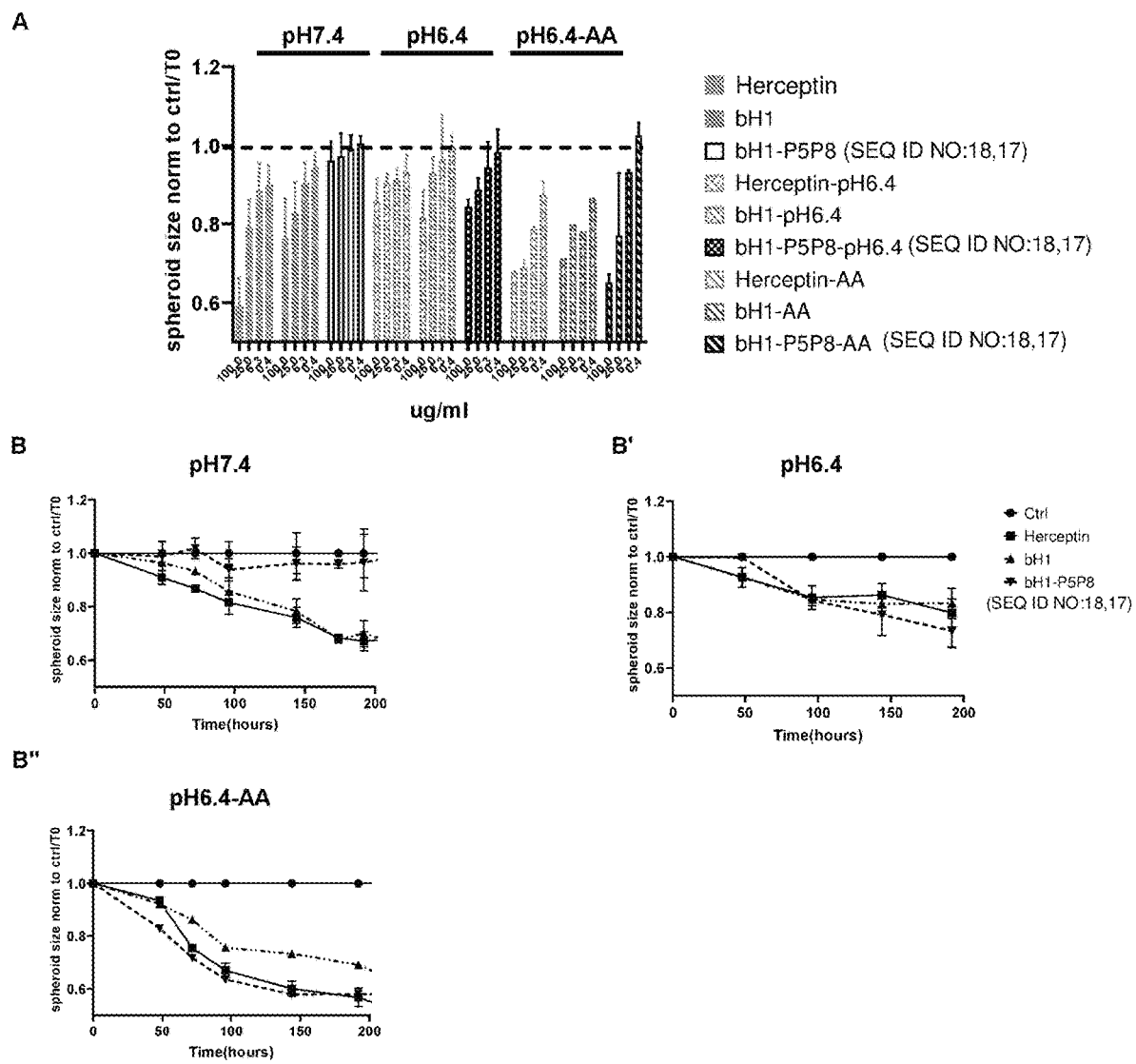
FIG. 11. The effect of Herceptin, bH1-FSA and its pH selective antibody variant bH1-P5P8-FSA on BT474 spheroid growth under normal and low pH conditions. A. Dose-response effect of antibodies at concentrations ranging from 100 µg/ml to 0.4 µg/ml was tested. Changes in spheroid size are reported as size normalized to isotype control human IgG and time zero for each concentration after 8 days of treatment in corresponding conditions at pH 7.4, pH 6.4 and pH 6.4-AA (acidosis adapted BT474 cells). B. Time course of change in spheroid size in response to 100 µg/ml of each antibody. Data is reported as normalized to control and time zero over 200 h at physiological pH of 7.4; or acute exposure to acidic pH of 6.4 (panel B'); or cells adapted to acidic pH of 6.4 (panel B").

We tested the pH-dependent function of the designed variant bH1-P5P8-FSA by evaluating its effect on the growth of the BT474 spheroids in vitro. We asked if the spheroids grown under normal or low-pH conditions respond differently to antibody treatment. We first established that the growth of the spheroids without antibody treatment in response to low pH conditions was not affected. To assess the pH selectivity of the designed antibody relative to Herceptin, spheroids were treated with different concentrations of antibodies either in physiological pH or a lower pH of 6.4 typical for solid tumor microenvironment (FIG. 11). As expected, Herceptin as well as the parental bH1 antibody inhibited growth at both pHs. The antibody mutant with engineered pH-sensitive Her2 binding only inhibited the growth when spheroids at low-pH conditions (FIGS. 11B' and 11B") but not at physiological pH (FIG. 11B). This suggests that the engineered pH selectivity for Her2 binding is also manifested functionally. The tumor growth inhibition efficacy of the engineered bH1-P5P8-FSA antibody was statistically indistinguishable from those of the benchmark Herceptin when the extracellular pH was acidified artificially (FIG. 11B') or when cells where adapted at the acidic pH (FIG. 11B").

Example 8: Cellular Internalization

BT474 mammary carcinoma cells were seeded at 6000 cells per well on black 96-well plate (Corning 4580) on the day prior to the assay. The media was then exchanged with the media containing 40 nM of the FITC conjugated antibodies and Hoechst for nuclei labeling diluted in pH 7.4 and pH 6.4 media followed by 4 h incubation at 37° C. The wells were then washed 3 times with cold PBS (+Ca and Mg). Fluorescent signal from membrane bound antibodies by addition of 1 mM Brilliant Black to the wells was then imaged immediately using ImageXpress micro XS with a 10× objective. Dual color imaging for nuclei in blue and green for the internalized antibodies were performed. Images were analyzed using the MetaXpress plate analysis platform (Molecular Devices). Each channel was first calibrated and a mask was created for the nuclei and internalized puncta. Nuclear area and FITC integrated intensity of the corresponding masked regions were measured. Integrated fluorescent intensity per nuclear area for each condition were reported.

Figure 12:
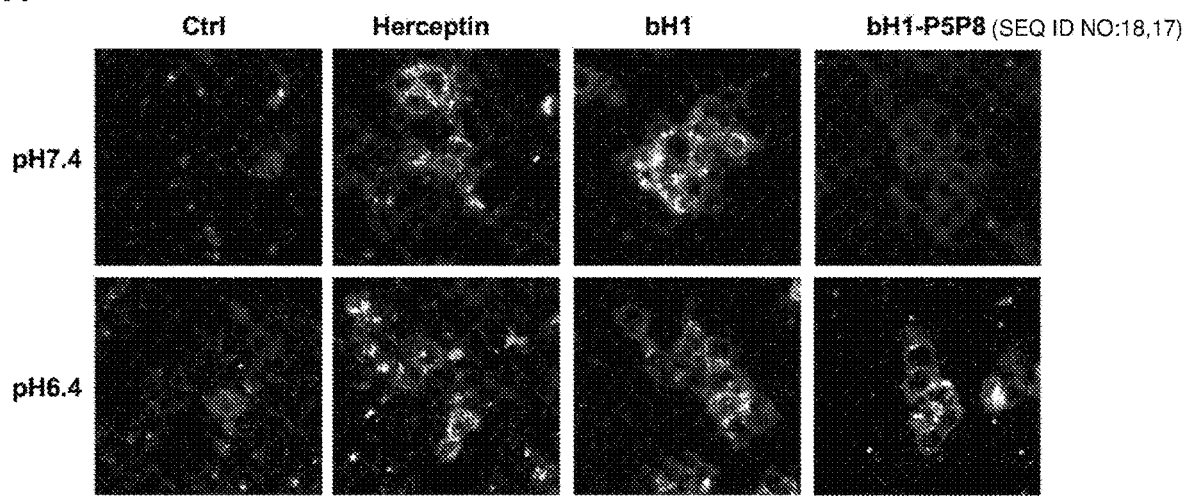
FIG. 12. Comparison of internalization capacity of Herceptin, bH1-FSA and its pH selective antibody variant bH1-P5P8-FSA in normal and low pH conditions. The internalization of FITC conjugated antibodies into BT474 cells was quantified under physiological pH of 7.4 or acidic pH of 6.4 conditions. A. Representative images for each pH condition. B. Quantified fluorescent intensity per cell area. Horizontal dashed lines indicate the level of internalization of the negative control antibody at each pH.
Figure 12:
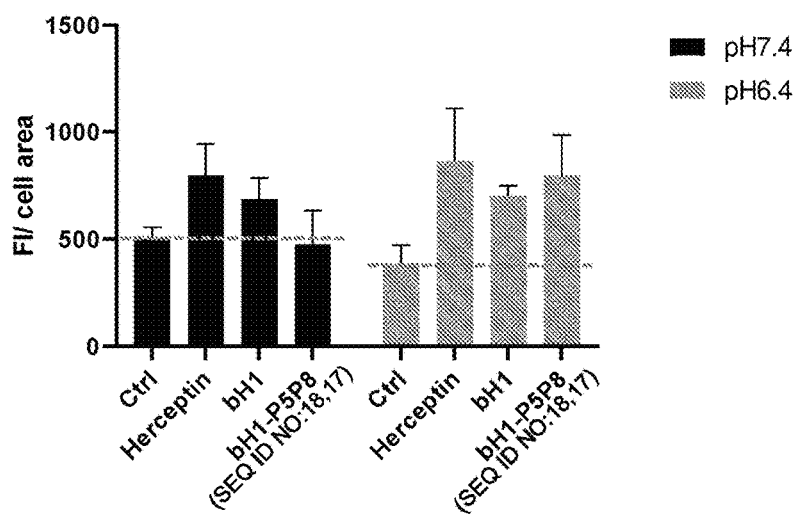

As shown in FIG. 12, the internalization of the pH-sensitive variants bH1-P5P8-FSA variant was similar to the negative control antibody at physiological pH, whereas its internalization was increased twice relative to the negative control at the acidic pH of 6.4 (FIG. 12B). This level of internalization at acidic pH was not statistically different than the internalization levels of Herceptin and parental bH1-FSA antibodies (FIG. 12B). In contrast to the pH sensitive antibody, increased levels of internalization relative to the negative control antibody were observed for Herceptin and the parental bH1-FSA antibodies at physiological pH of 7.4 (FIG. 12B). These results corroborate with the cell binding data described in Example 4 and growth inhibition functional data described in Example 7.

Example 9: Cellular Efficacy as Antibody-Drug Conjugates

Figure 13:
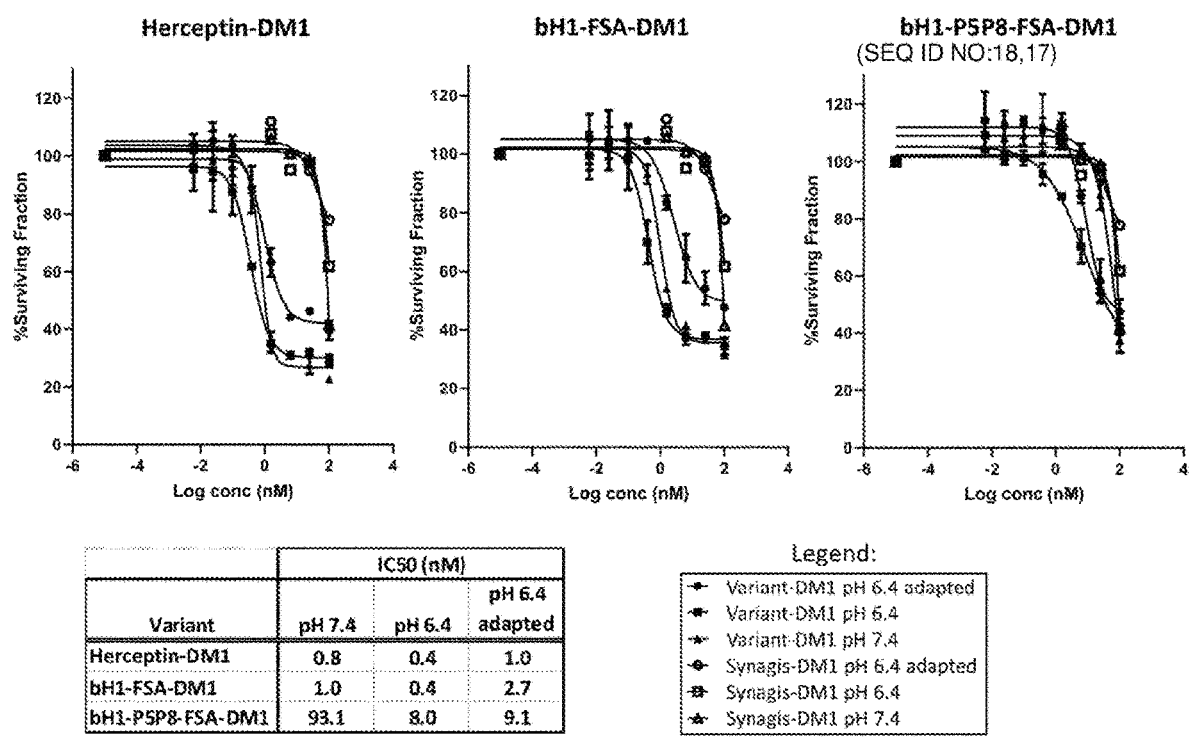
FIG. 13. ADC efficacy of DM1-conjugated antibody variants in BT474 cells at pH 7.4 versus pH 6.4.

Herein it is further demonstrated that treatment of BT474 cancer cells with pH-dependent mutant antibody, conjugated to the maytansine drug DM1 (bH1-P5P8-FSA-DM1), results in improved ADC efficacy under acidic conditions compared to physiological pH. BT474 cells were seeded onto 96-well culture plates and then treated with increasing doses of antibody-drug conjugates (ADCs): Herceptin-DM1, bH1-FSA-DM1, bH1-P5P8-FSA-DM1 or non-specific antibody control, Synagis-DM1, in either pH 7.4 or pH 6.4 buffered media at 37° C. for 13.5 days. In addition, BT474 cells that had been previously adapted to acidosis (pH 6.4 adapted), were treated with these ADCs in pH 6.4 medium. Growth inhibition, relative to growth of non-treated cells, was measured by monitoring cell confluency normalized to time zero, using Incucyte live cell analysis. FIG. 13 shows growth inhibition curves for cells treated with each ADC variant at the different pH conditions, compared to the Synagis-DM1 controls, and a table of derived IC50 values. The Herceptin-DM1 and parent bH1-FSA-DM1 ADCs have similar potencies at both pH 7.4 and pH 6.4 (IC50 range 0.4-2.7 nM). In contrast, at pH 7.4, mutant bH1-P5P8-FSA-DM1 showed low potency (IC50~93 nM), that was within the range of Synagis-DM1 background (IC50~90-100 nM), but had ~10-fold higher potency at pH 6.4 in acidosis-adapted and non-adapted cells (IC50~8-9 nM).

TABLE 3

Apparent binding affinities to SKOV3 cells for bH1 variants formatted as Fab fragments.

| Variants | SEQ ID NO | Physiological pH (7.3) $K_D$ $[10^{-9}M]$ | Acidic pH (5.2) $K_D$ $[10^{-9}M]$ |
|---|---|---|---|
| bH1-Fab | | 21.3 | ~41 [a] |
| bH1-P5-Fab | 14, 15 | NBD | ~199 [a] |
| bH1-P5P7-Fab | 14, 16 | NBD | ~178 [a] |
| bH1-P5P8-Fab | 14, 17 | NBD | ~93 [a] |

[a] Approximate values since $B_{max}$ was not reached.
NB: no binding detected.

As seen in Table 3, in SKOV3 cells, i.e., cells that express Her2 at a density of ~200,000 molecules/cell, the novel bH1 variants have a relatively weaker binding in an acidic pH relative to the parent bH1 Fab; however, these designed Fab variants have no binding at a physiological pH which would advantageously reduce binding to Her2-expressing cells in the physiological pH microenvironment of normal cells. In contrast, the parental bH1 Fab binds potently to these

TABLE 1

Computational predictions of relative binding affinities and stabilities under acidic and physiological conditions.

| | | | $\Delta G_{Acidic}^{Mutant} - \Delta G_{Acidic}^{Parent}$ | | | $\Delta\Delta\Delta G$ Binding | | | | |
|---|---|---|---|---|---|---|---|---|---|---|
| Variant | Mutation | CDR loop | Stability FoldX$_S$ | Binding FoldX$_B$ | SIE | Rosetta | Stability FoldXs | FoldX$_B$ | SIE | Rosetta | Consensus Rank |
| bH1-P1 | H-N28H | H1 | 0.91 | 0.00 | -0.25 | 0.75 | 0.69 | 0.05 | -0.38 | -0.08 | 6 |
| bH1-P2 | H-Y33H | H1 | 1.60 | 0.01 | 0.08 | 0.60 | 0.00 | -0.72 | 0.01 | 0.05 | 30 |
| bH1-P3 | H-R50H | H2 | 3.56 | 1.30 | 1.35 | 2.15 | -0.65 | -6.68 | -1.88 | 0.00 | NA[a] |
| bH1-P4 | H-Y56H | H2 | 0.43 | 0.00 | -0.37 | 0.75 | 0.00 | -0.92 | -0.23 | 0.25 | 10 |
| bH1-P5 | H-R58H | H2 | 0.74 | 0.42 | -0.40 | -0.13 | -0.10 | -0.06 | -0.11 | -0.48 | 2 |
| bH1-P6 | H-Y100aH | H3 | 1.02 | 0.04 | 0.11 | 0.76 | 0.00 | -1.71 | -0.61 | 0.90 | 8 |
| bH1-P7 | L-R30aH | L1 | 1.62 | -0.01 | 0.18 | 0.50 | 0.13 | -0.26 | -0.06 | -0.24 | 1 |
| bH1-P8 | L-S30bH | L1 | -0.07 | 0.00 | 0.15 | 0.21 | 0.03 | 0.49 | 0.00 | -0.08 | 26 |

[a]Top ranked if the stability filter under acidic condition (FoldX$_S$ >2.7 kcal/mol) is not applied.

TABLE 2

SPR data for Fab binding to recombinant human Her2 ectodomain

| | | Physiological pH (7.4) | | | | Acidic pH (5.0) | | | | |
|---|---|---|---|---|---|---|---|---|---|---|
| Variant | Mutation | $K_D$ (SD) $[10^{-9}M]$ | $k_{on}$ (SD) $[10^5 M^{-1}s^{-1}]$ | $k_{off}$ (SD) $[10^{-3}s^{-1}]$ | n | $K_D$ (SD) $[10^{-9}M]$ | $k_{on}$ (SD) $[10^5 M^{-1}s^{-1}]$ | $k_{off}$ (SD) $[10^{-3}s^{-1}]$ | n | $\Delta\Delta\Delta G_{binding}$ [kcal/mol] |
| bH1 | Parent | 3.0 (1.0) | 5.0 (2.0) | 1.4 (0.07) | 12 | 13 (4.0) | 2.5 (0.5) | 3.3 (0.6) | 15 | 0.00 |
| bH1-P1 | H-N28H | 3.5 (0.2) | 3.7 (0.2) | 1.3 (0.01) | 5 | 16 (2.0) | 1.9 (0.4) | 2.8 (0.4) | 5 | 0.02 |
| bH1-P2 | H-Y33H | 120 (3.0) | 1.7 (0.3) | 20 (3.0) | 5 | 1200 (400) | 0.4 (0.1) | 48 (8.0) | 5 | 0.49 |
| bH1-P3 | H-R50H | NB | NB | NB | 1 | NB | NB | NB | 1 | NB |
| bH1-P4 | H-Y56H | 170 | 7.8 | 130 | 1 | NB | NB | NB | 1 | NB |
| bH1-P5 | H-R58H | 310 (8.0) | 0.5 (0.01) | 16 (0.7) | 6 | 98 (30) | 0.9 (0.3) | 8.0 (1.0) | 14 | -1.54 |
| bH1-P6 | H-Y100aH | 10 (0.5) | 4.8 (0.3) | 4.8 (0.04) | 2 | ND | ND | ND | 2 | ND |
| bH1-P7 | L-R30aH | 5.7 (0.3) | 3.3 (0.3) | 1.9 (0.09) | 5 | 17 (1.0) | 1.6 (0.1) | 2.8 (0.3) | 5 | -0.21 |
| bH1-P8 | L-S30bH | 3.4 (0.1) | 3.4 (0.2) | 1.2 (0.01) | 5 | 9.9 (0.9) | 1.6 (0.2) | 1.5 (0.3) | 5 | -0.23 |
| bH1-P5P7 | H-R58H, L-R30aH | 530 (80) | 0.4 (0.1) | 21 (2.0) | 6 | 90 (20) | 0.7 (0.1) | 5.7 (0.3) | 8 | -1.93 |
| bH1-P5P8 | H-R58H, L-S30bH | 290 (50) | 0.4 (0.1) | 11 (1.0) | 8 | 50 (20) | 0.9 (0.4) | 3.7 (0.3) | 10 | -1.91 |

SD: standard deviation.
n: number of replicates.
NB: no binding.
ND: not determined due to poor fit.

Her2-expressing cells at the physiological pH, which is indicative of potential toxicity to normal tissues.

As listed in Table 5, similar biophysical properties for all bH1-FSA variants at both pH 5.1 and pH 7.2. All variants

TABLE 4

Apparent binding affinities to SKOV3 cells for bH1 variants formatted as full-size antibodies (FSAs).

| Variants | SEQ ID NO | pH 7.3 $K_D$ $[10^{-9}M]$ | pH 6.8 $K_D$ $[10^{-9}M]$ | pH 6.4 $K_D$ $[10^{-9}M]$ | pH 6.0 $K_D$ $[10^{-9}M]$ | pH 5.6 $K_D$ $[10^{-9}M]$ | pH 5.2 $K_D$ $[10^{-9}M]$ |
|---|---|---|---|---|---|---|---|
| bH1-FSA |  | 4.1 | 2.0 | 2.9 | 2.9 | 1.5 | 2.6 |
| bH1-P5-FSA | 18, 15 | ~176[a] | 15.7 | 12.9 | 10.9 | 8.0 | 7.8 |
| bH1-P5P7-FSA | 18, 16 | ~716[a] | 29.7 | 16.0 | 9.7 | 9.5 | 8.4 |
| bH1-P5P8-FSA | 18, 17 | ~290[a] | 21.7 | 15.1 | 9.7 | 6.6 | 12.3 |
| Herceptin [b] |  | 3.0 | ND | ND | ND | ND | 2.5 |

[a] Approximate values since $B_{max}$ was not reached.
[b] Herceptin FSA included for comparative purposes at the extreme pH values tested only (ND: not determined).

As provided in Table 4, in SKOV3 cells, i.e., cells that express Her2 at a density of ~200,000 molecules/cell, the novel bH1 variants formatted as FSAs have a slightly weaker binding in an acidic pH in the range 5.2-6.8 relative to the parent bH1 FSA and the related FSA Herceptin; however, the designed FSA variants disclosed in this application have a much weaker binding at a physiological pH of 7.3, which would advantageously reduce binding to Her2-expressing cells in the physiological pH microenvironment of normal cells. In contrast, the parental bH1 FSA and Herceptin bind potently to these Her2-expressing cells at the physiological pH with a similar affinity to that exhibited at acidic pH, which suggests potential toxicity to normal tissues. The antibody variants now provided, as shown above, provide an at least 10-fold increase in binding affinity/selectivity at an acidic pH, for example, $K_D$ in an acidic pH environment is at least 10-fold lower than $K_D$ in a physiological pH physiological environment. As exemplified above, the $K_D$ of the provided novel FSA variants is lower in an acidic pH environment typically surrounding solid tumor cells (for example, $K_D$ below 50 nM) when compared to the $K_D$ in a physiological pH physiological environment typical for normal cells.

behave similarly in each buffer. The SV data shows that for each variant in each buffer, the major peak accounting for 84-90% of the total peak area is at 6.4-6.5S, consistent with monomeric antibody. Each variant has a minor peak at 8-10S, consistent with dimeric antibody, accounting for 3-6% of the total peak area. The DSC data shows that for each variant $T_m1$ (CH2-domain melting) occurs at ~65° C. in acetate buffer and at ~70° C. in DPBS. Comparing results in acetate buffer and DPBS, $T_m2$ (Fab melting) and $T_m3$ (CH3-domain melting) differ by ~2 degrees and 1 degree, respectively, for each variant. Since generally the designed antibody variants behave similarly to the parental bH1-FSA antibody and they appear more stable at physiological pH than acidic pH, their observed decrease in antigen binding at physiological pH is not due to thermal destabilization or aggregation.

TABLE 5

Summary of biophysical characterization of bH1-FSA variants by DSC and SV.

| Variants | SEQ ID NO | Sedimentation velocity (SV) | | | | Differential scanning calorimetry (DSC) | | |
|---|---|---|---|---|---|---|---|---|
|  |  | pH 7.2 (DPBS) | | pH 5.1 (Acetate) | | | pH 7.2 (DPBS) | pH 5.1 (Acetate) |
|  |  | S | peak % | S | peak % | $T_m$ | ° C. | ° C. |
| bH1-FSA |  | 6.43 | 87.9 | 6.41 | 89.3 | 1 | 71.2 | 65.2 |
|  |  | 8.84 | 5.6 | 9.05 | 5.7 | 2 | 76.0 | 74.3 |
|  |  | >10 | 3.6 | >10 | 3.3 | 3 | 83.2 | 82.8 |
| bH1-P5-FSA | 18, 15 | 6.46 | 89.8 | 6.40 | 88.7 | 1 | 70.7 | 65.5 |
|  |  | 9.27 | 6.0 | 8.63 | 6.0 | 2 | 77.7 | 75.4 |
|  |  | >10 | 4.2 | >10 | 2.3 | 3 | 84.0 | 83.1 |
| bH1-P5P7-FSA | 18, 16 | 6.51 | 86.9 | 6.50 | 87.5 | 1 | 70.4 | 65.5 |
|  |  | 10.29 | 4.4 | 9.07 | 5.4 | 2 | 78.2 | 75.6 |
|  |  | >11 | 8.5 | >10 | 1.1 | 3 | 84.3 | 83.2 |
| bH1-P5P8-FSA | 18, 17 | 6.50 | 84.5 | 6.40 | 91.5 | 1 | 70.7 | 65.6 |
|  |  | 9.65 | 5.0 | 8.89 | 4.4 | 2 | 77.4 | 74.9 |
|  |  | >10 | 9.0 | >10 | 1.2 | 3 | 83.9 | 83.0 |

TABLE 6

Sequence listing.

| Name (CDR definition) | Chain | SEQ ID NO: | Sequence (illustrative examples of signal peptides are underlined, if present) |
|---|---|---|---|
| CDR-H1 (Kabat + Chothia) | Heavy | 1 | GFNIKDTYIH |
| CDR-H2 (Kabat) | Heavy | 2 | RIYPTNGYTHYADSVKG |
| CDR-H3 (Kabat) | Heavy | 3 | WGGDGFYAMDY |
| CDR-L1-generic (Kabat) | Light | 4 | RASQDIPX$_1$X$_2$ISGYVA |
| CDR-L2 (Kabat) | Light | 5 | WGSYLYS |
| CDR-L3 (Kabat) | Light | 6 | QQHYTTPPT |
| CDR-L1-v1 (Kabat) | Light | 7 | RASQDIPRSISGYVA |
| CDR-L1-v2 (Kabat) | Light | 8 | RASQDIPHSISGYVA |
| CDR-L1-v3 (Kabat) | Light | 9 | RASQDIPRHISGYVA |
| bH1-P5-Fv | Heavy | 10 | EVQLVESGGGLVQPGGSLRLSCAASGFNIKDTYIHWVRQAPGKGLEWVARIYPTNGYTHYADSVKGRFTISADTSKNTAYLQMNSLRAEDTAVYYCSRWGGDGFYAMDYWGQGTLVTVSS |
|  | Light | 11 | DIQMTQSPSSLSASVGDRVTITCRASQDIPRSISGYVAWYQQKPGKAPKLLIYWGSYLYSGVPSRFSGSGSGTDFTLTISSLQPEDFATYYCQQHYTTPPTFGQGTKVEIK |
| bH1-P5P7-Fv | Heavy | 10 | EVQLVESGGGLVQPGGSLRLSCAASGFNIKDTYIHWVRQAPGKGLEWVARIYPTNGYTHYADSVKGRFTISADTSKNTAYLQMNSLRAEDTAVYYCSRWGGDGFYAMDYWGQGTLVTVSS |
|  | Light | 12 | DIQMTQSPSSLSASVGDRVTITCRASQDIPHSISGYVAWYQQKPGKAPKLLIYWGSYLYSGVPSRFSGSGSGTDFTLTISSLQPEDFATYYCQQHYTTPPTFGQGTKVEIK |
| bH1-P5P8-Fv | Heavy | 10 | EVQLVESGGGLVQPGGSLRLSCAASGFNIKDTYIHWVRQAPGKGLEWVARIYPTNGYTHYADSVKGRFTISADTSKNTAYLQMNSLRAEDTAVYYCSRWGGDGFYAMDYWGQGTLVTVSS |
|  | Light | 13 | DIQMTQSPSSLSASVGDRVTITCRASQDIPRHISGYVAWYQQKPGKAPKLLIYWGSYLYSGVPSRFSGSGSGTDFTLTISSLQPEDFATYYCQQHYTTPPTFGQGTKVEIK |
| bH1-P5-Fab | Heavy | 14 | <u>MDWTWRILFLVAAATGTHA</u>EVQLVESGGGLVQPGGSLRLSCAASGFNIKDTYIHWVRQAPGKGLEWVARIYPTNGYTHYADSVKGRFTISADTSKNTAYLQMNSLRAEDTAVYYCSRWGGDGFYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKT |
|  | Light | 15 | <u>MVLQTQVFISLLLWISGAYG</u>DIQMTQSPSSLSASVGDRVTITCRASQDIPRSISGYVAWYQQKPGKAPKLLIYWGSYLYSGVPSRFSGSGSGTDFTLTISSLQPEDFATYYCQQHYTTPPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| bH1-P5P7-Fab | Heavy | 14 | <u>MDWTWRILFLVAAATGTHA</u>EVQLVESGGGLVQPGGSLRLSCAASGFNIKDTYIHWVRQAPGKGLEWVARIYPTNGYTHYADSVKGRFTISADTSKNTAYLQMNSLRAEDTAVYYCSRWGGDGFYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKT |
|  | Light | 16 | <u>MVLQTQVFISLLLWISGAYG</u>DIQMTQSPSSLSASVGDRVTITCRASQDIPHSISGYVAWYQQKPGKAPKLLIYWGSYLYSGVPSRFSGSGSGTDFTLTISSLQPEDFATYYCQQHYTTPPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| bH1-P5P8-Fab | Heavy | 14 | <u>MDWTWRILFLVAAATGTHA</u>EVQLVESGGGLVQPGGSLRLSCAASGFNIKDTYIHWVRQAPGKGLEWVARIYPTNGYTHYADSVKGRFTISADTSKNTAYLQMNSLRAEDTAVYYCSRWGGDGFYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKT |
|  | Light | 17 | <u>MVLQTQVFISLLLWISGAYG</u>DIQMTQSPSSLSASVGDRVTITCRASQDIPRHISGYVAWYQQKPGKAPKLLIYWGSYLYSGVPSRFSGSGSGTDFTLTISSLQPEDFATYYCQQHYTTPPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

TABLE 6-continued

Sequence listing.

| Name (CDR definition) | Chain | SEQ ID NO: | Sequence (illustrative examples of signal peptides are underlined, if present) |
|---|---|---|---|
| bH1-P5-FSA | Heavy | 18 | <u>MDWTWRILFLVAAATGTHA</u>EVQLVESGGGLVQPGGSLRLSCAASGENIKDTYIHWVRQAPGK GLEWVARIYPTNGYTHYADSVKGRFTISADTSKNTAYLQMNSLRAEDTAVYYCSRWGGDGFY AMDYWGQGTLVTVSSASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVDKKVEPKSCDKTHTC PPCPAPELLGGPSVFLEPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFELYSKLTV DKSRWQQGNVFSCSVMHEALHNHYTQKSLSLSPG |
| | Light | 15 | <u>MVLQTQVFISLLLWISGAYG</u>DIQMTQSPSSLSASVGDRVTITCRASQDIPRSISGYVAWYQQ KPGKAPKLLIYWGSYLYSGVPSRFSGSGSGTDFTLTISSLQPEDFATYYCQQHYTTPPTFGQ GTKVEIKRTVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| bH1-P5P7-FS | Heavy | 18 | <u>MDWTWRILFLVAAATGTHA</u>EVQLVESGGGLVQPGGSLRLSCAASGENIKDTYIHWVRQAPGK GLEWVARIYPTNGYTHYADSVKGRFTISADTSKNTAYLQMNSLRAEDTAVYYCSRWGGDGFY AMDYWGQGTLVTVSSASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVDKKVEPKSCDKTHTC PPCPAPELLGGPSVFLEPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFELYSKLTV DKSRWQQGNVFSCSVMHEALHNHYTQKSLSLSPG |
| | Light | 16 | <u>MVLQTQVFISLLLWISGAYG</u>DIQMTQSPSSLSASVGDRVTITCRASQDIPHSISGYVAWYQQ KPGKAPKLLIYWGSYLYSGVPSRFSGSGSGTDFTLTISSLQPEDFATYYCQQHYTTPPTFGQ GTKVEIKRTVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| bH1-P5P8-FSA | Heavy | 18 | <u>MDWTWRILFLVAAATGTHA</u>EVQLVESGGGLVQPGGSLRLSCAASGENIKDTYIHWVRQAPGK GLEWVARIYPTNGYTHYADSVKGRFTISADTSKNTAYLQMNSLRAEDTAVYYCSRWGGDGFY AMDYWGQGTLVTVSSASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVDKKVEPKSCDKTHTC PPCPAPELLGGPSVFLEPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFELYSKLTV DKSRWQQGNVFSCSVMHEALHNHYTQKSLSLSPG |
| | Light | 17 | <u>MVLQTQVFISLLLWISGAYG</u>DIQMTQSPSSLSASVGDRVTITCRASQDIPRHISGYVAWYQQ KPGKAPKLLIYWGSYLYSGVPSRFSGSGSGTDFTLTISSLQPEDFATYYCQQHYTTPPTFGQ GTKVEIKRTVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| bH1-P5-Fv (DNA) | Heavy | 19 | GAGGTGCAGCTGGTGGAGAGCGGCGGCGGCCTGGTGCAGCCCGGCGGCAGCCTGAGACTGAG CTGCGCCGCCAGCGGCTTCAACATCAAGGACACCTACATCCACTGGGTGAGACAGGCCCCCG GCAAGGGCCTGGAGTGGGTGGCCAGAATCTACCCCACCAACGGCTACACCCACTACGCCGAC AGCGTGAAGGGCAGATTCACCATCAGCGCCGACACCAGCAAGAACACCGCCTACCTGCAGAT GAACAGCCTGAGAGCCGAGGACACCGCCGTGTACTACTGCAGCAGATGGGGCGGCGACGGCT TCTACGCCATGGACTACTGGGGCCAGGGCACCCTGGTGACCGTGAGCAGC |
| | Light | 20 | GACATCCAGATGACCCAGAGCCCCAGCAGCCTGAGCGCCAGCGTGGGCGACAGAGTGACCAT CACCTGCAGAGCCAGCCAGGACATCCCCAGAAGCATCAGCGGCTACGTGGCCTGGTACCAGC AGAAGCCCGGCAAGGCCCCCAAGCTGCTGATCTACTGGGGCAGCTACCTGTACAGCGGCGTG CCCAGCAGATTCAGCGGCAGCGGCAGCGGCACCGACTTCACCCTGACCATCAGCAGCCTGCA GCCCGAGGACTTCGCCACCTACTACTGCCAGCAGCACTACACCACCCCCCCCACCTTCGGCC AGGGCACCAAGGTGGAGATCAAG |
| bH1-P5P7-Fv (DNA) | Heavy | 19 | GAGGTGCAGCTGGTGGAGAGCGGCGGCGGCCTGGTGCAGCCCGGCGGCAGCCTGAGACTGAG CTGCGCCGCCAGCGGCTTCAACATCAAGGACACCTACATCCACTGGGTGAGACAGGCCCCCG GCAAGGGCCTGGAGTGGGTGGCCAGAATCTACCCCACCAACGGCTACACCCACTACGCCGAC AGCGTGAAGGGCAGATTCACCATCAGCGCCGACACCAGCAAGAACACCGCCTACCTGCAGAT GAACAGCCTGAGAGCCGAGGACACCGCCGTGTACTACTGCAGCAGATGGGGCGGCGACGGCT TCTACGCCATGGACTACTGGGGCCAGGGCACCCTGGTGACCGTGAGCAGC |
| | Light | 21 | GACATCCAGATGACCCAGAGCCCCAGCAGCCTGAGCGCCAGCGTGGGCGACAGAGTGACCAT CACCTGCAGAGCCAGCCAGGACATCCCCCACAGCATCAGCGGCTACGTGGCCTGGTACCAGC AGAAGCCCGGCAAGGCCCCCAAGCTGCTGATCTACTGGGGCAGCTACCTGTACAGCGGCGTG CCCAGCAGATTCAGCGGCAGCGGCAGCGGCACCGACTTCACCCTGACCATCAGCAGCCTGCA GCCCGAGGACTTCGCCACCTACTACTGCCAGCAGCACTACACCACCCCCCCCACCTTCGGCC AGGGCACCAAGGTGGAGATCAAG |

TABLE 6-continued

Sequence listing.

| Name (CDR definition) | Chain | SEQ ID NO: | Sequence (illustrative examples of signal peptides are <u>underlined</u>, if present) |
|---|---|---|---|
| bH1-P5P8-Fv (DNA) | Heavy | 19 | GAGGTGCAGCTGGTGGAGAGCGGCGGCGGCCTGGTGCAGCCCGGCGGCAGCCTGAGACTGAG<br>CTGCGCCGCCAGCGGCTTCAACATCAAGGACACCTACATCCACTGGGTGAGACAGGCCCCCG<br>GCAAGGGCCTGGAGTGGGTGGCCAGAATCTACCCCACCAACGGCTACACCCACTACGCCGAC<br>AGCGTGAAGGGCAGATTCACCATCAGCGCCGACACCAGCAAGAACACCGCCTACCTGCAGAT<br>GAACAGCCTGAGAGCCGAGGACACCGCCGTGTACTACTGCAGCAGATGGGGCGGCGACGGCT<br>TCTACGCCATGGACTACTGGGGCCAGGGCACCCTGGTGACCGTGAGCAGC |
| | Light | 22 | GACATCCAGATGACCCAGAGCCCCAGCAGCCTGAGCGCCAGCGTGGGCGACAGAGTGACCAT<br>CACCTGCAGAGCCAGCCAGGACATCCCCAGACACATCAGCGGCTACGTGGCCTGGTACCAGC<br>AGAAGCCCGGCAAGGCCCCCAAGCTGCTGATCTACTGGGGCAGCTACCTGTACAGCGGCGTG<br>CCCAGCAGATTCAGCGGCAGCGGCAGCGGCACCGACTTCACCCTGACCATCAGCAGCCTGCA<br>GCCCGAGGACTTCGCCACCTACTACTGCCAGCAGCACTACACCACCCCCCCCACCTTCGGCC<br>AGGGCACCAAGGTGGAGATCAAG |

REFERENCES

All patents, patent applications and publications referred to herein and throughout the application are hereby incorporated by reference.

REFERENCES

1. Sampson, J. H., et al., *Tumor-specific immunotherapy targeting the EGFRvIII mutation in patients with malignant glioma.* Semin Immunol, 2008. 20(5): p. 267-75.
2. Slaga, D., et al., *Avidity-based binding to HER2 results in selective killing of HER2-overexpressing cells by anti-HER2/CD3.* Sci Transl Med, 2018. 10(463).
3. Rudnick, S. I., et al., *Influence of affinity and antigen internalization on the uptake and penetration of Anti-HER2 antibodies in solid tumors.* Cancer Res, 2011. 71(6): p. 2250-9.
4. Harms, B. D., et al., *Optimizing properties of antireceptor antibodies using kinetic computational models and experiments.* Methods Enzymol, 2012. 502: p. 67-87.
5. Zhou, Y., et al., *Impact of intrinsic affinity on functional binding and biological activity of EGFR antibodies.* Mol Cancer Ther, 2012. 11(7): p. 1467-76.
6. Tannock, I. F. and D. Rotin, *Acid pH in tumors and its potential for therapeutic exploitation.* Cancer Res, 1989. 49(16): p. 4373-84.
7. Stubbs, M., et al., *Causes and consequences of tumour acidity and implications for treatment.* Mol Med Today, 2000. 6(1): p. 15-9.
8. Kato, Y., et al., *Acidic extracellular microenvironment and cancer.* Cancer Cell Int, 2013. 13(1): p. 89.
9. Zhang, X., Y. Lin, and R. J. Gillies, *Tumor pH and its measurement.* J Nucl Med, 2010. 51(8): p. 1167-70.
10. Damaghi, M., J. W. Wojtkowiak, and R. J. Gillies, *pH sensing and regulation in cancer.* Front Physiol, 2013. 4: p. 370.
11. Hashim, A. I., et al., *Imaging pH and metastasis.* NMR Biomed, 2011. 24(6): p. 582-91.
12. Gillies, R. J., et al., *MRI of the tumor microenvironment.* J Magn Reson Imaging, 2002. 16(4): p. 430-50.
13. Estrella, V., et al., *Acidity generated by the tumor microenvironment drives local invasion.* Cancer Res, 2013. 73(5): p. 1524-35.
14. Fukamachi, T., et al., *Tumor specific low pH environments enhance the cytotoxicity of lovastatin and cantharidin.* Cancer Lett, 2010. 297(2): p. 182-9.
15. Tanokura, M., *1H-NMR study on the tautomerism of the imidazole ring of histidine residues. I. Microscopic pK values and molar ratios of tautomers in histidine-containing peptides.* Biochim Biophys Acta, 1983. 742(3): p. 576-85.
16. Igawa, T., F. Mimoto, and K. Hattori, *pH-dependent antigen-binding antibodies as a novel therapeutic modality.* Biochim Biophys Acta, 2014. 1844(11): p. 1943-1950.
17. Schroter, C., et al., *A generic approach to engineer antibody pH-switches using combinatorial histidine scanning libraries and yeast display.* MAbs, 2015. 7(1): p. 138-51.
18. Konning, D., et al., *Isolation of a pH-sensitive IgNAR variable domain from a yeast-displayed, histidine-doped masterlibrary.* Mar Biotechnol (NY), 2016. 18(2): p. 161-7.
19. Tillotson, B. J., et al., *Engineering an anti-transferrin receptor scFv for pH-sensitive binding leads to increased intracellular accumulation.* PLoS One, 2015. 10(12): p. e0145820.
20. Igawa, T., et al., *Antibody recycling by engineered pH-dependent antigen binding improves the duration of antigen neutralization.* Nat Biotechnol, 2010. 28(11): p. 1203-7.
21. Murtaugh, M. L., et al., *A combinatorial histidine scanning library approach to engineer highly pH-dependent protein switches.* Protein Sci, 2011. 20(9): p. 1619-31.
22. Chaparro-Riggers, J., et al., *Increasing serum half-life and extending cholesterol lowering in vivo by engineering antibody with pH-sensitive binding to PCSK9.* J Biol Chem, 2012. 287(14): p. 11090-7.
23. Devanaboyina, S. C., et al., *The effect of pH dependence of antibody-antigen interactions on subcellular trafficking dynamics.* MAbs, 2013. 5(6): p. 851-9.
24. Bonvin, P., et al., *De novo isolation of antibodies with pH-dependent binding properties.* MAbs, 2015. 7(2): p. 294-302.
25. Sarkar, C. A., et al., *Rational cytokine design for increased lifetime and enhanced potency using pH-activated "histidine switching".* Nat Biotechnol, 2002. 20(9): p. 908-13.
26. Heinzelman, P., et al., *Engineering pH responsive fibronectin domains for biomedical applications.* J Biol Eng, 2015. 9: p. 6.
27. Traxlmayr, M. W., et al., *Construction of pH-sensitive Her2-binding IgG1-Fc by directed evolution.* Biotechnol J, 2014. 9(8): p. 1013-22.

28. Bailey, L. J., et al., *Applications for an engineered Protein-G variant with a pH controllable affinity to antibody fragments*. J Immunol Methods, 2014. 415: p. 24-30.
29. Gera, N., et al., *Design of pH sensitive binding proteins from the hyperthermophilic Sso7d scaffold*. PLoS One, 2012. 7(11): p. e48928.
30. Strauch, E. M., S. J. Fleishman, and D. Baker, *Computational design of a pH-sensitive IgG binding protein*. Proc Natl Acad Sci USA, 2014. 111(2): p. 675-80.
31. Tsukamoto, M., et al., *Engineered protein A ligands, derived from a histidine-scanning library, facilitate the affinity purification of IgG under mild acidic conditions*. J Biol Eng, 2014. 8: p. 15.
32. Seijsing, J., et al., *An engineered affibody molecule with pH-dependent binding to FcRn mediates extended circulatory half-life of a fusion protein*. Proc Natl Acad Sci USA, 2014. 111(48): p. 17110-5.
33. Ghetie, V., et al., *Increasing the serum persistence of an IgG fragment by random mutagenesis*. Nat Biotechnol, 1997. 15(7): p. 637-40.
34. Lippow, S. M., K. D. Wittrup, and B. Tidor, *Computational design of antibody-affinity improvement beyond in vivo maturation*. Nat Biotech, 2007. 25(10): p. 1171-1176.
35. Vivcharuk, V., et al., *Assisted Design of Antibody and Protein Therapeutics (ADAPT)*. PloS one, 2017. 12(7): p. e0181490.
36. Spassov, V. Z. and L. Yan, *pH-selective mutagenesis of protein-protein interfaces: in silico design of therapeutic antibodies with prolonged half-life*. Proteins, 2013. 81(4): p. 704-14.
37. Bostrom, J., et al., *Variants of the antibody herceptin that interact with HER2 and VEGF at the antigen binding site*. Science, 2009. 323(5921): p. 1610-4.
38. Sulea, T., et al., *Application of Assisted Design of Antibody and Protein Therapeutics (ADAPT) improves efficacy of a Clostridium difficile toxin A single-domain antibody*. Sci Rep, 2018. 8(1): p. 2260.
39. Kabat, E. A. and T. T. Wu, *Identical V region amino acid sequences and segments of sequences in antibodies of different specificities. Relative contributions of VH and VL genes, minigenes, and complementarity-determining regions to binding of antibody-combining sites*. J Immunol, 1991. 147(5): p. 1709-19.
40. Chothia, C. and A. M. Lesk, *Canonical structures for the hypervariable regions of immunoglobulins*. J Mol Biol, 1987. 196(4): p. 901-917.
41. Lefranc, M. P., et al., *IMGT unique numbering for immunoglobulin and T cell receptor variable domains and Ig superfamily V-like domains*. Dev Comp Immunol, 2003. 27(1): p. 55-77.
42. Brinkmann, U. and R. E. Kontermann, *The making of bispecific antibodies*. MAbs, 2017. 9(2): p. 182-212.
43. Spiess, C., Q. Zhai, and P. J. Carter, *Alternative molecular formats and therapeutic applications for bispecific antibodies*. Mol Immunol, 2015. 67(2 Pt A): p. 95-106.
44. Kontermann, R. E., *Dual targeting strategies with bispecific antibodies*. MAbs, 2012. 4(2): p. 182-97.
45. Eisenberg, D., et al., *Analysis of membrane and surface protein sequences with the hydrophobic moment plot*. J Mol Biol, 1984. 179(1): p. 125-42.
46. Kelley, R. F. and M. P. O'Connell, *Thermodynamic analysis of an antibody functional epitope*. Biochemistry, 1993. 32(27): p. 6828-6835.
47. Bostrom, J., et al., *High affinity antigen recognition of the dual specific variants of herceptin is entropy-driven in spite of structural plasticity*. PLoS One, 2011. 6(4): p. e17887.
48. Dotti, G., et al., *Design and development of therapies using chimeric antigen receptor-expressing T cells*. Immunol Rev, 2014. 257(1): p. 107-26.
49. Zhang, J., et al., *Pentamerization of single-domain antibodies from phage libraries: a novel strategy for the rapid generation of high-avidity antibody reagents*. J Mol Biol, 2004. 335(1): p. 49-56.
50. Merritt, E. A. and W. G. Hol, *AB5 toxins*. Curr Opin Struct Biol, 1995. 5(2): p. 165-71.
51. de Kruif, J. and T. Logtenberg, *Leucine zipper dimerized bivalent and bispecific scFv antibodies from a semi-synthetic antibody phage display library*. J Biol Chem, 1996. 271(13): p. 7630-4.
52. Ridgway, J. B., L. G. Presta, and P. Carter, *'Knobs-into-holes' engineering of antibody CH3 domains for heavy chain heterodimerization*. Protein Eng, 1996. 9(7): p. 617-21.
53. Krivov, G. G., M. V. Shapovalov, and R. L. Dunbrack, Jr., *Improved prediction of protein side-chain conformations with SCWRL4*. Proteins, 2009. 77(4): p. 778-95.
54. Naim, M., et al., *Solvated interaction energy (SIE) for scoring protein-ligand binding affinities. 1. Exploring the parameter space*. J Chem Inf Model, 2007. 47(1): p. 122-133.
55. Sulea, T. and E. O. Purisima, *The solvated interaction energy method for scoring binding affinities*. Methods Mol Biol, 2012. 819: p. 295-303.
56. Guerois, R., J. E. Nielsen, and L. Serrano, *Predicting changes in the stability of proteins and protein complexes: a study of more than 1000 mutations*. J Mol Biol, 2002. 320(2): p. 369-387.
57. Schymkowitz, J., et al., *The FoldX web server: an online force field*. Nucleic Acids Res, 2005. 33(Web Server issue): p. W382-8.
58. O Conchuir, S., et al., *A web resource for standardized benchmark datasets, metrics, and Rosetta protocols for macromolecular modeling and design*. PLoS One, 2015. 10(9): p. e0130433.
59. Rohl, C. A., et al., *Protein structure prediction using Rosetta*. Methods Enzymol, 2004. 383: p. 66-93.
60. Sulea, T., et al., *Assessment of solvated interaction energy function for ranking antibody-antigen binding affinities*. J Chem Inf Model, 2016. 56(7): p. 1292-303.
61. Onsum, M. D., et al., *Single-cell quantitative HER2 measurement identifies heterogeneity and distinct subgroups within traditionally defined HER2-positive patients*. Am J Pathol, 2013. 183(5): p. 1446-1460.
62. Beck, A., et al., *Strategies and challenges for the next generation of antibody-drug conjugates*. Nat Rev Drug Discov, 2017. 16(5): p. 315-337.
63. Masters, J. C., et al., *Clinical toxicity of antibody drug conjugates: a meta-analysis of payloads*. Invest New Drugs, 2018. 36(1): p. 121-135.
64. Nelson, A. L., *Antibody fragments: hope and hype*. MAbs, 2010. 2: p. 77-83.

WO2012075581
WO2012100346
WO2008027236
WO2010027981
WO2010108127
WO2015095539
WO1995004069
WO2004076670
WO2003046560

The invention claimed is:

1. An anti-Her2 antibody or antigen-binding fragment thereof comprising a heavy chain complementarity determining region 1 (CDR-H1) comprising the amino acid sequence GFNIKDTYIH (SEQ ID NO:1), a CDR-H2 comprising the amino acid sequence RIYPTNGYTHYADSVKG (SEQ ID NO:2), a CDR-H3 comprising the amino acid sequence WGGDGFYAMDY (SEQ ID NO: 3), a light chain complementarity determining region 1 (CDR-L1) comprising the amino acid sequence RASQDIPX$_1$X$_2$ISGYVA (SEQ ID NO:4), a CDR-L2 comprising sequence the amino acid WGSYLYS (SEQ ID NO:5) and a CDR-L3 comprising the amino acid sequence QQHYTTPPT (SEQ ID NO:6); wherein: X$_1$ is R or H, and X$_2$ is S or H.

2. The antibody or antigen-binding fragment thereof of claim 1, wherein SEQ ID NO: 4 comprises a sequence selected from the group consisting of SEQ ID NO:7, SEQ ID NO:8 and SEQ ID NO:9.

3. The antibody or antigen-binding fragment thereof of claim 1 comprising a heavy-chain variable sequence comprising SEQ ID NO:10; and a light-chain variable sequence comprising a sequence selected from the group consisting of SEQ ID NO:11, SEQ ID NO:12 and SEQ ID NO:13.

4. The antibody or antigen-binding fragment thereof of claim 1, which binds Her2-expressing cells selectively at a pH between 5.0 and 6.8 relative to a pH between 7.2 and 7.4.

5. The antibody or antigen-binding fragment thereof of claim 4, which:
binds Her2-expressing cells with at least 10-fold increased selectivity at a pH between 5.0 and 6.8 relative to at a pH between 7.2 and 7.4;
inhibits growth of Her2-expressing cells selectively at a pH of 6.4 relative to at a pH of 7.4; and/or
internalizes into Her2-expressing cells selectively at a pH of 6.4 relative to at a pH of 7.4.

6. The antibody or antigen-binding fragment thereof of claim 1, wherein the antibody or antigen-binding fragment thereof is a bivalent full-size antibody or a Fab.

7. The antibody or antigen-binding fragment thereof of claim 6, wherein the antibody comprises a constant region of human origin.

8. The antibody or antigen-binding fragment thereof of claim 6, comprising an amino acid sequence selected from the group consisting of SEQ ID NO:14, SEQ ID NO:15, SEQ ID NO:16, SEQ ID NO:17 and SEQ ID NO:18.

9. The antibody or antigen-binding fragment thereof of claim 1, wherein the antibody or antigen-binding fragment thereof is in the form of a scFv, di-scFv, Fab, Fab', F(ab')2, a multimer thereof, or a bi-specific T-cell engager.

10. The antibody or antigen-binding fragment thereof of claim 1, wherein the antibody or antigen-binding fragment thereof is: comprised in a protein fusion, in a chimeric antigen receptor (CAR), or in a multivalent or multispecific display format.

11. A nucleic acid molecule encoding the antibody or antigen-binding fragment thereof of claim 1.

12. The antibody or antigen-binding fragment thereof of claim 1, wherein the antibody or antigen-binding fragment thereof is immobilized onto a surface.

13. The antibody or antigen-binding fragment thereof of claim 1, wherein the antibody or antigen-binding fragment thereof is linked to a cargo molecule.

14. A composition comprising one or more than one antibody or antigen-binding fragment thereof of claim 1 and a pharmaceutically-acceptable carrier, diluent, or excipient.

15. A cell expressing a nucleic acid encoding the antibody or antigen-binding fragment thereof of claim 1.

16. A method of treating Her2 expressing solid tumors, comprising administering the antibody or antigen-binding fragment thereof of claim 1 to a subject in need thereof.

17. A method of detecting Her2 expressing solid tumors, comprising administering the antibody or fragment thereof of claim 1 to a subject, wherein the antibody or antigen binding fragment thereof is linked to a detectable agent, and detecting the antibody or fragment thereof using a suitable detection and/or imaging technology.

18. A method of capturing the Her2 ectodomain, comprising contacting a sample with one or more than one antibody or antigen-binding fragment thereof of claim 12, and allowing the Her2 ectodomain to bind to the antibody or fragment thereof in a pH of between 5.0 and 6.8, and releasing the Her2 ectodomain from the antibody or antigen-binding fragment thereof by raising the pH to between 7.2 and 7.4.

19. The antibody or antigen-binding fragment thereof of claim 1, wherein the antibody comprises a constant region of human origin.

20. The antibody or antigen-binding fragment thereof of claim 1, comprising an amino acid sequence selected from the group consisting of SEQ ID NO:14, SEQ ID NO:15, SEQ ID NO:16, SEQ ID NO:17 and SEQ ID NO:18.

\* \* \* \* \*